(12) United States Patent
Yanagi et al.

(10) Patent No.: US 6,440,586 B1
(45) Date of Patent: Aug. 27, 2002

(54) BENZOPYRAN COMPOUND, MATERIAL FOR LUMINOUS DEVICE, AND LUMINOUS DEVICE USING THE SAME

(75) Inventors: Terukazu Yanagi; Hisashi Okada; Tatsuya Igarashi, all of Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/533,240

(22) Filed: Mar. 22, 2000

(30) Foreign Application Priority Data

Mar. 26, 1999 (JP) .......................... 11-083250
Apr. 9, 1999 (JP) .......................... 11-102752
Aug. 24, 1999 (JP) .......................... 11-237265

(51) Int. Cl.$^7$ ............................. H05B 33/12
(52) U.S. Cl. .................. 428/690; 428/917; 313/504; 313/506
(58) Field of Search ................ 428/690, 704, 428/917; 313/504, 506; 252/301.16; 544/245, 298, 309, 310, 311; 548/301.7; 546/112, 152, 159, 171

(56) References Cited

U.S. PATENT DOCUMENTS 5,281,489 A * 1/1994 Mori et al. .................. 428/690

FOREIGN PATENT DOCUMENTS

| JP | 50-135118 | * 10/1975 | |
| JP | 5-169853 | * 7/1993 | |
| JP | 6-228544 | 8/1994 | ........... C09K/11/06 |

* cited by examiner

*Primary Examiner*—Marie Yamnitzky
(74) *Attorney, Agent, or Firm*—Sughrue Mion, PLLC

(57) ABSTRACT

A compound for a luminous device represented by (I), (I-a), (III) or (I'):

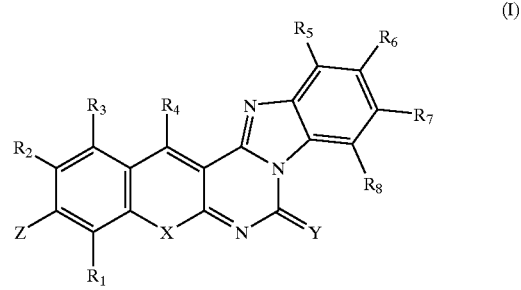

(I)

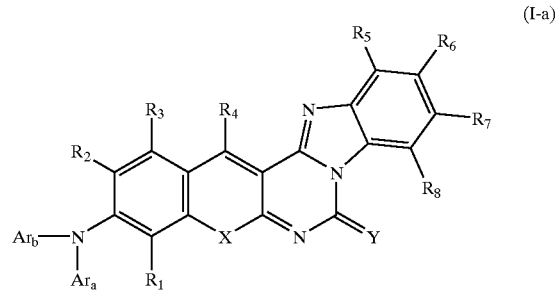

(I-a)

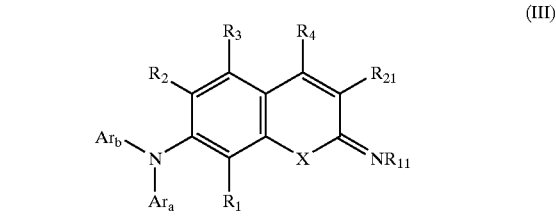

(III)

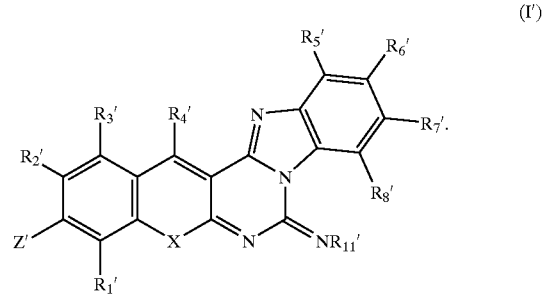

(I')

4 Claims, No Drawings

BENZOPYRAN COMPOUND, MATERIAL FOR LUMINOUS DEVICE, AND LUMINOUS DEVICE USING THE SAME

FIELD OF THE INVENTION

The present invention relates to a compound suitable for use for a filter dye, a color conversion filter, a photographic material, a sensitizing dye, a dye for pulp-dyeing, a laser dye, a fluorescent medicine for a medical diagnosis, a luminous device, etc. Particularly, the present invention relates to a material for a luminous device for use in planar light sources and displays, and to a luminous device of high luminance. More specifically, the invention relates to the luminous material capable of emitting sharp green to red light of high luminance, high luminous efficiency and high color purity with low voltage application, and to a luminous device using the luminous material.

BACKGROUND OF THE INVENTION

Prospects of a luminous device in which organic materials are used are promising as a solid luminescent type inexpensive and large area full color display device and development has been tried variously. A luminous device generally comprises a pair of counter electrodes and a luminous layer interposed between the electrodes. When an electric field is impressed between the electrodes, electrons are injected from the cathode and positive holes are injected from the anode, and the electrons and positive holes are recombined in the luminous layer. A phenomenon of emitting energy as light when energy level is returned from conduction band to valence band is luminescence.

Luminous devices so far been used require high driving voltage and emission luminance and luminous efficiency are low, and characteristic deterioration is remarkable, so have not been put to practical use yet. An organic luminous device comprising lamination of thin layers containing an organic compound having high fluorescent quantum efficiency capable of emitting light with low voltage of 10 V or lower has been reported (*Applied Physics Letters*, Vol. 51, p. 913 (1987)) and attracting public attention in recent years. According to this technique, high luminance green light emission can be obtained by using a metal chelate complex as the electron-transporting layer, a fluorescent band layer as the luminous layer, and an amine compound as the positive hole-transporting layer, as a result, luminance has reached several 1,000 cd/m$^2$ with direct current voltage of 6 to 7 V. However, further improvement of luminance and development of luminous device of high luminous efficiency have been required in the light of a practical luminous device. Further, when taking into consideration the utilization of a luminous device as a full color display and a light source, it is necessary to get three primary colors or a white color in practical use. A device capable of emitting a desired color by doping a fluorescent dye is reported (*Journal of Applied Physics*, Vol. 65, p. 3610 (1989)). This technique is particularly effective for red luminescence in which extinction due to concentration is large and a fluorescent dye alone is used with difficulty as the luminous layer, and high color purity and high luminance have been attained in red luminescence. However, when a device doped with a dye is produced by deposition, there have been problems such that characteristics of devices are difficult to be reproduced from the aspect of its manufacturing process and that since the durability of the dye is low, the luminance is reduced or the color changes after being used for a long period of time. To cope with these problems, development of the material which functions as an electric charge-transporting material and a luminous material in one has been desired. However, with materials so far been developed, when a fluorescent dye is used in high concentration as an electric charge-transporting material, there have been problems that emission with high luminance is difficult as extinction due to concentration and that characteristics of devices are deteriorated due to agglomeration of the fluorescent dye with the lapse of time. Therefore, from the viewpoint of the simplification of producing step and the stability of performance of a device, a luminous material having good color purity and capable of using a dye alone as the luminous layer, in particular, a non-doping type luminous material capable of attaining good chromaticity and luminance even when a dye is used alone as the luminous layer has so far been desired.

On the other hand, luminous devices which have realized high luminance emission are laminated devices formed by vacuum deposition of organic materials, but from the viewpoint of simplification of producing step, processability, and realization of large area devices, it is desired to produce devices by a coating system. However, devices produced by a coating system so far been used are inferior to those produced by a vapor deposition system in luminance and luminous efficiency, therefore, high luminance and luminescence with high efficiency have been left as the problems to be solved. In addition, with devices produced by coating an organic low molecular weight compound dispersed in a polymer binder, uniform planar luminescence for a long period of time is difficult due to the agglomeration of the organic low molecular weight compound.

Further, in recent years, various materials having fluorescence have been used for a filter dye, a color conversion filter, a dye for a photographic material, a sensitizing dye, a dye for pulp-dyeing, a laser dye, a fluorescent medicine for a medical diagnosis, a material for a luminous device, etc., and demand for such materials has been increased. However, compounds having high fluorescent color purity and high fluorescent intensity are less, therefore, the development of a novel material has been desired.

SUMMARY OF THE INVENTION

A first object of the present invention is to provide a material for a luminous device capable of emitting light with high luminance and high efficiency, excellent in stability at repeated use, and capable of uniform and planar emission with low voltage driving, and to provide a luminous device using the material.

A second object of the present invention is to provide a compound having high fluorescent intensity and high fluorescent color purity.

A third object of the present invention is to provide a luminous material capable of attaining emission with high luminance and high luminous efficiency even in the form of non-doping type, and to provide a luminous device using the material.

A fourth object of the present invention is to provide a material for a luminous device having high luminescent color purity, and to provide a luminous device using the material.

Other objects and effects of the present invention will become more apparent from the following description.

The present invention relates to the following compounds:

a compound represented by formula (I):

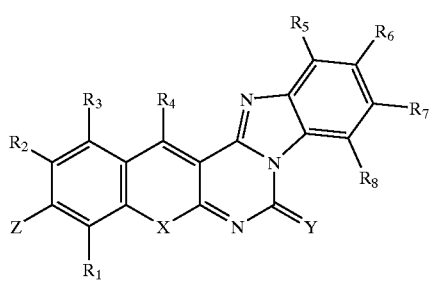

wherein $R_1$, $R_2$, $R_3$, $R_4$, $R_5$, $R_6$, $R_7$ and $R_8$ each represents a hydrogen atom or a substituent; X represents O, S or N—R, wherein R represents a hydrogen atom, an aliphatic hydrocarbon group, an aryl group or a heterocyclic group; Y represents O, S or $CQ_1(Q_2)$, wherein $Q_1$ and $Q_2$ each represents a hydrogen atom or a substituent, at least either one of them represents an electron attractive group, and $Q_1$ and $Q_2$ may be linked to each other to form a ring; and Z is represented by the following formula (II):

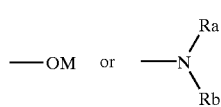

wherein $R_a$ and $R_b$ each represents a hydrogen atom, an aliphatic hydrocarbon group, an aryl group or a heterocyclic group, and at least one combination of $R_a$ and $R_b$, $R_a$ and $R_1$, and $R_b$ and $R_2$ may be linked to each other to form a ring; M represents a hydrogen atom, an aliphatic hydrocarbon group, an aryl group, a heterocyclic group or a cation;

a compound represented by formula (I-a):

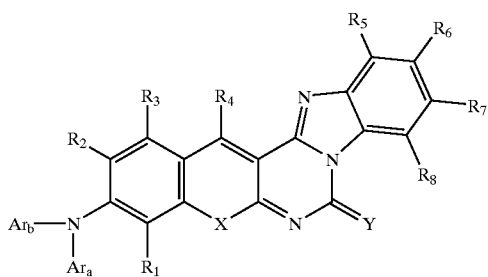

wherein $R_1$, $R_2$, $R_3$, $R_4$, $R_5$, $R_6$, $R_7$ and $R_8$ each represents a hydrogen atom or a substituent; X represents O, S or N—R, wherein R represents a hydrogen atom, an aliphatic hydrocarbon group, an aryl group or a heterocyclic group; $Ar_a$ and $Ar_b$ each represents an aryl group or an aromatic heterocyclic group, and at least one combination of $Ar_a$ and $Ar_b$, $Ar_a$ and $R_1$, and $Ar_b$ and $R_2$ may be linked to each other to form a ring; and Y represents O or S;

a compound represented by formula (III):

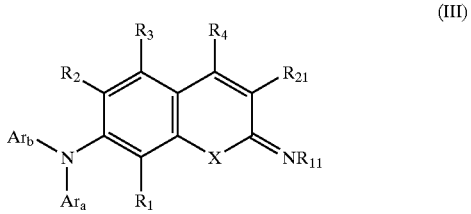

wherein $R_1$, R2, $R_3$ and $R_4$ each represents a hydrogen atom or a substituent; $R_{11}$ represents a hydrogen atom, an aliphatic hydrocarbon group, an aryl group or a heterocyclic group; $R_{21}$ represents a hydrogen atom or a substituent; X represents O, S or N—R, wherein R represents a hydrogen atom, an aliphatic hydrocarbon group, an aryl group or a heterocyclic group; and $Ar_a$ and $Ar_b$ each represents an aryl group or an aromatic heterocyclic group, and at least one combination of $Ar_a$ and $Ar_b$, $Ar_a$ and $R_1$, and $Ar_b$ and $R_2$ may be linked to each other to form a ring; and a compound represented by formula (I'):

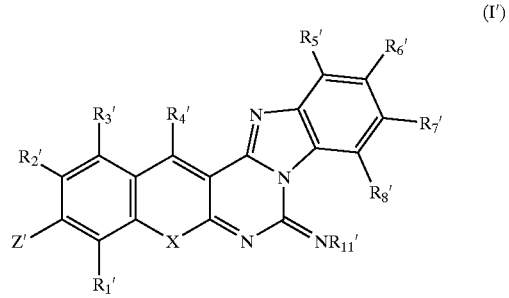

wherein $R_1'$, $R_2'$, $R_3'$, $R_4'$, $R_5'$, $R_6'$, $R_7'$, R8' and $R_{11}'$ each represents a hydrogen atom or a substituent; X' represents O, S or N—$R_1'$, wherein R' represents a hydrogen atom, an aliphatic hydrocarbon group, an aryl group or a heterocyclic group; and Z' represents N—$R_a'R_b'$ (wherein $R_a'$ and $R_b'$ each represents a hydrogen atom, an aliphatic hydrocarbon group, an aryl group or a heterocyclic grou) or —OM' (wherein M' represents a hydrogen atom, an aliphatic hydrocarbon group, an aryl group, a heterocyclic group or a cation).

The present invention also relates to a luminous material comprising a compound of formula (I), (I-a), (III) or (I').

The present invention further relates to a luminous device comprising:
- a pair of electrodes; and
- at least one organic compound thin layer including a luminous layer, provided between the electrodes,
- wherein at least one layer of said organic compound thin layer(s) contains at least one compound of formula (I), (I-a), (III) or (I').

Preferably, said at least one layer further comprises a polymer and said at least one compound of formula (I), (I-a), (III) or (I') is dispersed in the polymer.

DETAILED DESCRIPTION OF THE INVENTION

The compound represented by formula (I) is described in detail below.

$R_1$, $R_2$, $R_3$, $R_4$, $R_5$, $R_6$, $R_7$ and $R_8$ each represents a hydrogen atom or a substituent. Examples of the substituents represented by $R_1$, $R_2$, $R_3$, $R_4$, $R_5$, $R_6$, $R_7$ and $R_8$ include an alkyl group (preferably an alkyl group having from 1 to 20, more preferably from 1 to 12, and particularly preferably from 1 to 8, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 20, more preferably from 2 to 12, and particularly preferably from 2 to 8, carbon atoms, e.g., vinyl, allyl, 2-butenyl, 3-pentenyl), an alkynyl group (preferably an alkynyl group having from 2 to 20, more preferably from 2 to 12, and particularly preferably from 2 to 8, carbon atoms, e.g., propargyl, 3-pentynyl), an aryl group (preferably an aryl group having from 6 to 30, more preferably from 6 to 20, and particularly preferably from 6 to 12, carbon atoms, e.g., phenyl, p-methylphenyl, naphthyl), an amino group (preferably an amino group having from 0 to 20, more preferably from 0 to 12, and particularly preferably from 0 to 6, carbon atoms, e.g., amino, methylamino, dimethylamino, diethylamino, diphenylamino, dibenzylamino), an alkoxyl group (preferably an alkoxyl group having from 1 to 20, more preferably from 1 to 12, and particularly preferably from 1 to 8, carbon atoms, e.g., methoxy, ethoxy, butoxy), an aryloxy group (preferably an aryloxy group having from 6 to 20, more preferably from 6 to 16, and particularly preferably from 6 to 12, carbon atoms, e.g., phenyloxy, 2-naphthyloxy), an acyl group (preferably an acyl group having from 1 to 20, more preferably from 1 to 16, and particularly preferably from 1 to 12, carbon atoms, e.g., acetyl, benzoyl, formyl, pivaloyl), an alkoxycarbonyl group (preferably an alkoxycarbonyl group having from 2 to 20, more preferably from 2 to 16, and particularly preferably from 2 to 12, carbon atoms, e.g., methoxycarbonyl, ethoxycarbonyl), an aryloxycarbonyl group (preferably an aryloxycarbonyl group having from 7 to 20, more preferably from 7 to 16, and particularly preferably from 7 to 10, carbon atoms, e.g., phenyloxycarbonyl), an acyloxy group (preferably an acyloxy group having from 2 to 20, more preferably from 2 to 16, and particularly preferably from 2 to 10, carbon atoms, e.g., acetoxy, benzoyloxy), an acylamino group (preferably an acylamino group having from 2 to 20, more preferably from 2 to 16, and particularly preferably from 2 to 10, carbon atoms, e.g., acetylamino, benzoylamino), an alkoxycarbonylamino group (preferably an alkoxycarbonylamino group having from 2 to 20, more preferably from 2 to 16, and particularly preferably from 2 to 12, carbon atoms, e.g., methoxycarbonylamino), an aryloxycarbonylamino group (preferably an aryloxycarbonylamino group having from 7 to 20, more preferably from 7 to 16, and particularly preferably from 7 to 12, carbon atoms, e.g., phenyloxycarbonylamino), a sulfonylamino group (preferably a sulfonylamino group having from 1 to 20, more preferably from 1 to 16, and particularly preferably from 1 to 12, carbon atoms, e.g., methanesulfonylamino, benzene sulfonylamino), a sulfamoyl group (preferably a sulfamoyl group having from 0 to 20, more preferably from 0 to 16, and particularly preferably from 0 to 12, carbon atoms, e.g., sulfamoyl, methylsulfamoyl, dimethylsulfamoyl, phenyl sulfamoyl), a carbamoyl group (preferably a carbamoyl group having from 1 to 20, more preferably from 1 to 16, and particularly preferably from 1 to 12, carbon atoms, e.g., carbamoyl, methylcarbamoyl, diethylcarbamoyl, phenyl carbamoyl), an alkylthio group (preferably an alkylthio group having from 1 to 20, more preferably from 1 to 16, and particularly preferably from 1 to 12, carbon atoms, e.g., methylthio, ethylthio), an arylthio group (preferably an arylthio group having from 6 to 20, more preferably from 6 to 16, and particularly preferably from 6 to 12, carbon atoms, e.g., phenylthio), a sulfonyl group (preferably a sulfonyl group having from 1 to 20, more preferably from 1 to 16, and particularly preferably from 1 to 12, carbon atoms, e.g., mesyl, tosyl), a sulfinyl group (preferably a sulfinyl group having from 1 to 20, more preferably from 1 to 16, and particularly preferably from 1 to 12, carbon atoms, e.g., methanesulfinyl, benzenesulfinyl), a ureido group (preferably a ureido group having from 1 to 20, more preferably from 1 to 16, and particularly preferably from 1 to 12, carbon atoms, e.g., ureido, methylureido, phenylureido), a phosphoric acid amido group (preferably a phosphoric acid amido group having from 1 to 20, more preferably from 1 to 16, and particularly preferably from 1 to 12, carbon atoms, e.g., diethyl phosphoric acid amido, phenylphosphoric acid amido), a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group, a heterocyclic group (preferably a heterocyclic group having from 1 to 30, and more preferably from 1 to 12, carbon atoms; as hetero atoms, e.g., nitrogen, oxygen, sulfur, and specifically, e.g., imidazolyl, pyridyl, quinolyl, furyl, thienyl, piperidyl, morpholino, benzoxazolyl, benzimidazolyl, benzothiazolyl can be exemplified), and a silyl group (preferably a silyl group having from 3 to 40, more preferably from 3 to 30, and particularly preferably from 3 to 24, carbon atoms, e.g., trimethylsilyl, triphenylsilyl). These substituents may further be substituted. When there are two or more substituents, they may be the same or different. Substituents may be linked to each other to form a ring, if possible.

$R_1$, $R_2$ and R3 each preferably represents a hydrogen atom or an alkyl group, more preferably a hydrogen atom or a lower alkyl group, and particularly preferably a hydrogen atom.

$R_4$ preferably represents a hydrogen atom or an alkyl group, more preferably a hydrogen atom or a lower alkyl group, and particularly preferably a hydrogen atom or a methyl group.

$R_5$, $R_6$, $R_7$ and $R_8$ each preferably represents a hydrogen atom, an alkyl group, an aryl group, a halogen atom, a cyano group, a sulfonyl group, a heterocyclic group, or a benzene ring formed by the substituents by linking, more preferably a hydrogen atom, a lower alkyl group (e.g., methyl, ethyl, n-propyl, isopropyl, t-butyl, trifluoromethyl), an aryl group (e.g., phenyl, p-methylphenyl, naphthyl), a halogen atom or a cyano group, and still more preferably a hydrogen atom, a chlorine atom or a cyano group.

X represents O, S or N—R (wherein R represents a hydrogen atom, an aliphatic hydrocarbon group, an aryl group or a heterocyclic group).

The aliphatic hydrocarbon group represented by R is a straight chain, branched or cyclic alkyl group (preferably an alkyl group having from 1 to 30, more preferably from 1 to 20, and still more preferably from 1 to 12, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 30, more preferably from 2 to 20, and still more preferably from 2 to 12, carbon atoms, e.g., vinyl, allyl, 2-butenyl, 3-pentenyl), or an alkynyl group (preferably an alkynyl group having from 2 to 30, more preferably from 2 to 20, and still more preferably from 2 to 12, carbon atoms, e.g., propargyl, 3-pentynyl), preferably an alkyl group or an alkenyl group, and more preferably a methyl group, an ethyl group, a propyl group, a butyl group or an allyl group.

The aryl group represented by R is preferably a monocyclic or bicyclic aryl group having from 6 to 30 carbon atoms (e.g., phenyl, naphthyl), more preferably a phenyl group having from 6 to 20 carbon atoms, and still more preferably a phenyl group having from 6 to 12 carbon atoms.

The heterocyclic group represented by R is a 3- to 10-membered saturated or unsaturated heterocyclic ring containing at least one N, O or S atom, the heterocyclic ring may be monocyclic, or may further form a condensed ring with other ring.

The heterocyclic group represented by R is preferably a 5- or 6-membered aromatic heterocyclic group, more preferably a 5- or 6-membered aromatic heterocyclic group containing a nitrogen atom or a sulfur atom.

Specific examples of the heterocyclic rings include, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene, preferred examples include pyrrole, imidazole, pyrazole, pyridine, pyrazine, pyridazine, triazole, triazine, indole, indazole, thiadiazole, oxadiazole, quinoline, phthalazine, quinoxaline, quinazoline, cinnoline, tetrazole, thiazole, oxazole, benzimidazole, benzoxazole, benzothiazole, and benzotriazole, more preferred examples include imidazole, pyridine, quinoline, thiazole, oxazole, benzimidazole, benzoxazole, benzothiazole, and benzotriazole, and still more preferred are pyridine and quinoline.

The aliphatic hydrocarbon group, aryl group or heterocyclic group represented by R may have a substituent and the examples of the substituents of $R_1$ to $R_8$ described above can be applied. R preferably represents an alkyl group, an alkenyl group or an aryl group, more preferably an alkyl group or a phenyi group.

X preferably represents O or N—R, and more preferably represents O.

Y represents O, S or $CQ_1(Q_2)$ (wherein at least either $Q_1$ or $Q_2$ represents an electron attractive group). The substituents exemplified above as to $R_1$ to $R_8$ can be applied to the substituents represented by $Q_1$ and $Q_2$. The electron attractive group represented by $Q_1$ and $Q_2$ is a group having a Hammett's $\sigma_p$ value of 0 or more. Preferred examples thereof include a cyano group, a carbonyl group, a thiocarbonyl group, an aryl group, an aromatic heterocyclic group, a sulfonyl group, a carbamoyl group, a sulfamoyl group, a trifluoromethyl group, and a halogen atom, more preferred examples are a cyano group, a carbonyl group, a sulfonyl group, and a trifluoromethyl group, and still more preferred are a cyano group and a carbonyl group.

$Q_1$ and $Q_2$ may form a ring together with the carbon atoms to which they are bonded. Preferred examples of the rings formed by $Q_1$ and $Q_2$ include a 1-indanone nucleus, a 1,3-dicarbonyl nucleus, a pyrazolinone nucleus, a 2,4,6-triketohexahydropyrimidine nucleus (including a thioketone form), a 2-thio-2,4-thiazolidinedione nucleus, a 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, and a 2-imidazolin-5-one nucleus, more preferred are a 1-indanone nucleus, a 1,3-dicarbonyl nucleus, and a 2,4,6-triketohexahydropyrimidine nucleus (including a thioketone form), and particularly preferred are a 3-aryl-1-indanone nucleus, a cyclic 1,3-dicarbonyl nucleus, a barbituric acid derivative, and a 2-thiobarbituric acid derivative.

Y preferably represents O, S, $CQ_{1a}(Q_{2a})$ (wherein $Q_{1a}$ and $Q_{2a}$ each represents a substituent (those exemplified as to $R_1$ to R8 can be applied to the substituents represented by $Q_{1a}$ and $Q_{2a}$), and at least either one represents a cyano group or a carbonyl group), or a cyclic 1,3-dicarbonyl nucleus, more preferably O or S, and particularly preferably O.

Z represents a group represented by —$NR_a(R_b)$ or —OM; $R_a$ and $R_b$, which may be the same or different, each represents a hydrogen atom, an aliphatic hydrocarbon group, an aryl group or a heterocyclic group, and $R_a$ and $R_b$, and/or $R_a$ and $R_1$, and/or $R_b$ and $R_2$ may be linked to each other to form a ring, if possible; M represents a hydrogen atom, an aliphatic hydrocarbon group, an aryl group, a heterocyclic group, or a cation.

The aliphatic hydrocarbon group represented by $R_a$ and $R_b$ is a straight chain, branched or cyclic alkyl group (preferably an alkyl group having from 1 to 30, more preferably from 1 to 20, and still more preferably from 1 to 12, carbon atoms, e.g., methyl, ethyl, isopropyl, tert-butyl, n-octyl, n-decyl, n-hexadecyl, cyclopropyl, cyclopentyl, cyclohexyl), an alkenyl group (preferably an alkenyl group having from 2 to 30, more preferably from 2 to 20, and still more preferably from 2 to 12, carbon atoms, e.g., vinyl, allyl, 2-butenyl, 3-pentenyl), or an alkynyl group (preferably an alkynyl group having from 2 to 30, more preferably from 2 to 20, and still more preferably from 2 to 12, carbon atoms, e.g., propargyl, 3-pentynyl), preferably an alkyl group or an alkenyl group, and more preferably a methyl group, an ethyl group, a propyl group, a butyl group, an allyl group, or a condensed ring formed by $R_a$ and $R_b$ by linking with a benzene ring (e.g., a julolidine ring).

The aryl group represented by $R_a$ and $R_b$ is preferably a monocyclic or bicyclic aryl group having from 6 to 30 carbon atoms (e.g., phenyl, naphthyl), more preferably a phenyl group having from 6 to 20 carbon atoms, and still more preferably a phenyl group having from 6 to 12 carbon atoms. In addition, $R_a$ and $R_b$ may be linked to the benzene ring to form a condensed ring in the case where such a linkage is possible.

The heterocyclic group represented by $R_a$ and $R_b$ is a 3- to 10-membered saturated or unsaturated heterocyclic group containing at least one N, O or S atom, the heterocyclic group may be monocyclic, or may further form a condensed ring with other ring.

The heterocyclic group is preferably a 3- to 10-membered aromatic heterocyclic group containing at least one N, O or S atom, more preferably a 5- or 6-membered aromatic heterocyclic group, and still more preferably a 5- or 6-membered aromatic heterocyclic group containing a nitrogen atom or a sulfur atom.

Specific examples of the heterocyclic rings include, e.g., pyrrolidine, piperidine, piperazine, morpholine, thiophene, furan, pyrrole, imidazole, pyrazole, pyridine, pyrazine, pyridazine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, and tetraazaindene, preferred examples include thiophene, triazole, oxazole, piperidine, triazine, and quinoline, more preferred examples include thiophene, piperidine, triazine, and quinoline, and still more preferred is thiophene.

The aliphatic hydrocarbon group, aryl group or heterocyclic group represented by $R_a$ and $R_b$ may have a substituent, and the substituents exemplified above as to $R_1$ to $R_8$ can be applied.

$R_a$ and $R_b$ each preferably represents a hydrogen atom, an alkyl group, an aryl group, or an aromatic heterocyclic group. When the compound represented by formula (I) is used as a non-doping type luminous material, $R_a$ and $R_b$ each preferably represents an aryl group or an aromatic heterocyclic group, and more preferably an aryl group (preferably a monocyclic or bicyclic aryl group having from 6 to 30 carbon atoms, more preferably a phenyl group having from 6 to 20 carbon atoms, and still more preferably a phenyl group having from 6 to 12 carbon atoms). When the compound represented by formula (I) is used as a doping type luminous material, $R_a$ and $R_b$ each preferably represents a hydrogen atom or an alkyl group, more preferably represents an alkyl group, still more preferably an alkyl group having from 1 to 8 carbon atoms, and particularly preferably a methyl group or an ethyl group.

The aliphatic hydrocarbon group, aryl group, and heterocyclic group represented by M have the same meaning as the aliphatic hydrocarbon group, aryl group, and heterocyclic group represented by R in formula (I) respectively.

As the cation represented by M, for example, a metal cation (e.g., a lithium cation, a sodium cation, a potassium cation, a cesium cation, a magnesium cation, a calcium cation, an aluminum cation, a europium cation), and a quaternary ammonium ion (preferably having from 1 to 30, more preferably from 1 to 20, and still more preferably from 1 to 10, carbon atoms, e.g., a tetrabutylammmonium ion) can be exemplified. These metal cations may have ligands.

M preferably represents a hydrogen atom, an alkyl group, an aryl group, an alkali metal ion, an alkaline earth metal ion, an aluminum ion, a zinc ion, a europium ion, or a quaternary ammonium ion, more preferably a hydrogen atom, an alkyl group, or an aryl group, and still more preferably a hydrogen atom or a methyl group.

Z preferably represents —$NR_a(R_b)$

The compound represented by formula (I) is preferably represented by formula (I-a):

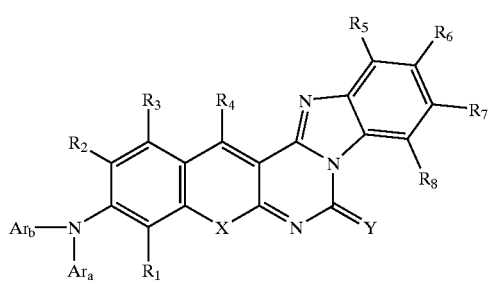

(I-a)

wherein $R_1$, $R_2$, $R_3$, $R_4$, $R_5$, $R_6$, $R_7$, $R_8$, X and Y have the same meaning as those in formula (I) respectively, and the respective preferred scopes are also the same; and $Ar_a$ and $Ar_b$ each represents an aryl group or an aromatic heterocyclic group, and the aryl group and the aromatic heterocyclic group have the same meaning as those represented by $R_a$ and $R_b$ in formula (I) respectively.

$Ar_a$ and $Ar_b$ each preferably represents an aryl group, more preferably a monocyclic or bicyclic aryl group having from 6 to 30 carbon atoms, still more preferably a phenyl group having from 6 to 20 carbon atoms, and particularly preferably a phenyl group having from 6 to 12 carbon atoms.

The compound represented by formula (I) is more preferably represented by formula (I-b):

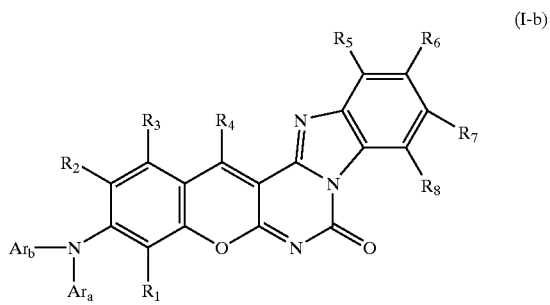

(I-b)

wherein $R_1$, $R_2$, $R_3$, $R_4$, $R_5$, $R_7$, $R_7$ and $R_8$ have the same meaning as those in formula (I) respectively, and the respective preferred scopes are also the same; and $Ar_a$ and $Ar_b$ each represents an aryl group or an aromatic heterocyclic group, and the aryl group and the aromatic heterocyclic group have the same meaning as those in formula (I-a) respectively, and the respective preferred scopes are also the same.

The compound represented by formula (III) is described in detail below.

$R_1$, $R_2$, $R_3$ and $R_4$ each represents a hydrogen atom or a substituent, they have the same meaning as those in formula (I) and the respective preferred scopes are also the same. X represents O, S or N—R (wherein R represents a hydrogen atom, an aliphatic hydrocarbon group, an aryl group or a heterocyclic group), they have the same meaning as those in formula (I) and the respective preferred scopes are also the same.

$Ar_a$ and $Ar_b$ each represents an aryl group or an aromatic heterocyclic group, and these aryl and aromatic heterocyclic groups have the same meaning as those in formula (I-a) respectively, and the respective preferred scopes are also the same.

$R_{11}$ represents a hydrogen atom, an aliphatic hydrocarbon group, an aryl group or a heterocyclic group, and $R_{11}$ has the same meaning as R in formula (I).

$R_{11}$ preferably represents a hydrogen atom, an alkyl group, or an aryl group, more preferably a hydrogen atom or an alkyl group having from 1 to 8 carbon atoms, still more preferably a hydrogen atom, a methyl group or an ethyl group, and particularly preferably a hydrogen atom.

$R_{21}$ represents a hydrogen atom or a substituent and has the same meaning as $R_1$ to $R_8$ in formula (I). $R_{21}$ preferably represents a hydrogen atom, an alkyl group, an aryl group, an acyl group, a carbonylamino group, a sulfonylamino group, a halogen atom, a cyano group, a sulfo group, a carboxyl group, a nitro group, a hydroxamic acid group, a sulfino group, a hydrazino group, an imino group, or a heterocyclic group, more preferably represents a hydrogen atom, an aryl group, an acyl group, a carbonylamino group, a sulfonylamino group, a halogen atom, a cyano group, a sulfo group, a carboxyl group, a nitro group, or an aromatic heterocyclic group, still more preferably a hydrogen atom, an acyl group, a carbonylamino group, a sulfonylamino group, a cyano group, a carboxyl group, a nitro group, or an aromatic heterocyclic group, particularly preferably a cyano group or an aromatic heterocyclic group, and most preferably an aromatic heterocyclic group.

The compound represented by formula (III) is preferably represented by formula (III-a):

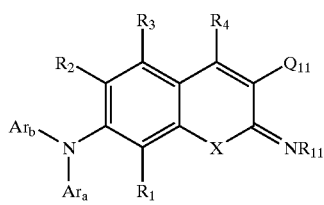

(III-a)

wherein $R_1$, $R_2$, $R_3$, $R_4$, $R_{11}$, X, $Ar_a$ and $Ar_b$ have the same meaning as those in formula (III) respectively, and the respective preferred scopes are also the same. $Q_{11}$ represents an atomic group necessary to form an aromatic heterocyclic ring. The aromatic heterocyclic group represented by $Q_{11}$ is a 3- to 10-membered aromatic heterocyclic group containing at least one N, O or S atom, which may be monocyclic, or may form a condensed ring together with other ring.

The aromatic heterocyclic group is preferably an aromatic heterocyclic group containing a nitrogen atom or a sulfur atom.

Specific examples of the aromatic heterocyclic rings include furan, thiophene, pyran, pyrrole, imidazole, pyrazole, pyridine, pyrazine, pyrimidine, pyridazine, thiazole, oxazole, isothiazole, isooxazole, thiadiazole, oxadiazole, triazole, tetrazole, quinoline, benzimidazole, benzoxazole, benzothiazole, and benzotriazole. The aromatic heterocyclic ring represented by $Q_{11}$ may further form a condensed ring, and may have a substituent. The substituents exemplified as to $R_1$ to $R_8$ in formula (I) can be applied.

The compound represented by formula (III) is more preferably represented by formula (III-b):

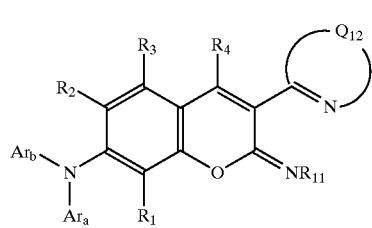

(III-b)

wherein $R_1$, $R_2$, $R_3$, $R_4$, $R_{11}$, $Ar_a$ and $Ar_b$ have the same meaning as those in formula (III-a) respectively, and the respective preferred scopes are also the same. $Q_{12}$ represents an atomic group necessary to form a nitrogen-containing aromatic heterocyclic ring. The nitrogen-containing aromatic heterocyclic ring formed by $Q_{12}$ may further form a condensed ring, and may have a substituent. The substituents exemplified as to $R_1$ to $R_8$ in formula (I) can be applied. The ring formed by $Q_{12}$ is preferably a 5- or 6-membered nitrogen-containing aromatic heterocyclic ring, more preferably a 5-membered nitrogen-containing aromatic heterocyclic ring. Specific examples of the nitrogen-containing aromatic heterocyclic rings include pyrrole, imidazole, pyrazole, pyridine, pyrazine, pyrimidine, pyridazine, thiazole, oxazole, isothiazole, isooxazole, thiadiazole, oxadiazole, triazole, tetrazole, quinoline, benzimidazole, benzoxazole, benzothiazole, and benzotriazole, preferably thiazole, oxazole, isothiazole, isooxazole, thiadiazole, oxadiazole, triazole, tetrazole, benzimidazole, benzoxazole, and benzothiazole.

The compound represented by formula (III) is still more preferably represented by formula (III-c):

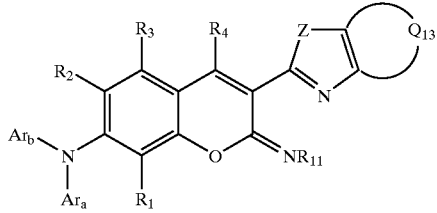

(III-c)

wherein $R_1$, $R_2$, $R_3$, $R_4$, $R_{11}$, $Ar_a$ and $Ar_b$ have the same meaning as those in formula (III-a) respectively, and the respective preferred scopes are also the same. $Q_{13}$ represents an atomic group necessary to form an aromatic heterocyclic ring or an aromatic hydrocarbon ring. The aromatic heterocyclic ring or the aromatic hydrocarbon ring formed by $Q_{13}$ may further form a condensed ring, and may have a substituent. The substituents exemplified as to $R_1$ to $R_8$ in formula (I) can be applied. Z represents O, S or N—$R_{31}$ (wherein $R_{31}$ represents a hydrogen atom, an aliphatic hydrocarbon group, an aryl group or a heterocyclic group, and has the same meaning as R in formula (I)).

As the aromatic heterocyclic rings formed by $Q_{13}$, preferred are those described as the specific examples of the aromatic heterocyclic rings in formula (III-a) and more preferred are pyridine and pyrazine. As the aromatic hydrocarbon rings formed by $Q_{13}$, preferred is a monocyclic or bicyclic aromatic hydrocarbon ring having from 6 to 30 carbon atoms, more preferred is an aromatic hydrocarbon ring having from 6 to 20 carbon atoms, and still more preferred is an aromatic hydrocarbon ring having from 6 to 12 carbon atoms. As the rings formed by $Q_{13}$, preferred are those described as the specific examples of the aromatic heterocyclic rings in formula (III-a) or a benzene ring having from 6 to 12 carbon atoms, more preferred are pyridine, pyrazine and benzene, and still more preferred is a benzene.

Z represents O, S or N—$R_{31}$ (wherein $R_{31}$ represents a hydrogen atom, an aliphatic hydrocarbon group, an aryl group or a heterocyclic group, and has the same meaning as R in formula (I)). $R_{31}$ preferably represents a hydrogen atom, an alkyl group, an aryl group, or an aromatic heterocyclic group, more preferably a hydrogen atom, an alkyl group or an aryl group, still more preferably a hydrogen atom, an alkyl group having from 1 to 8 carbon atoms, or a phenyl group having from 6 to 12 carbon atoms, and particularly preferably a hydrogen atom, a methyl group, an ethyl group, or a phenyl group.

Z preferably represents O, S or N—$R_{32}$ (wherein $R_{32}$ represents a hydrogen atom, a methyl group, an ethyl group, or a phenyl group), and more preferably represents N—$R_{32}$.

The compounds represented by formulae (I), (I-a), (I-b), (III), (III-a), (III-b) and (III-c) may be low molecular weight compounds, or may be high molecular weight compounds having the residue bonding to the polymer main chain (preferably having a weight average molecular weight of from 1,000 to 5,000,000, more preferably from 5,000 to 2,000,000, and still more preferably from 10,000 to 1,000,000), or may be high molecular weight compounds having the compounds according to the present invention at the main chain (preferably having a weight average molecular weight of from 1,000 to 5,000,000, more preferably from 5,000 to 2,000,000, and still more preferably from 10,000 to 1,000,000). The high molecular weight compounds may be homopolymers or copolymers with other polymers, and the copolymers may be random copolymers or block copolymers. The compounds for use in the present invention are preferably low molecular weight compounds. Further, the above formulae take limiting structures for convenience sake but the compounds may be tautomers thereof.
Specific examples of the compounds represented by formula (I) are shown below but the present invention is not limited thereto.
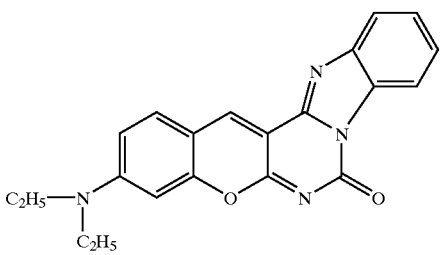
1
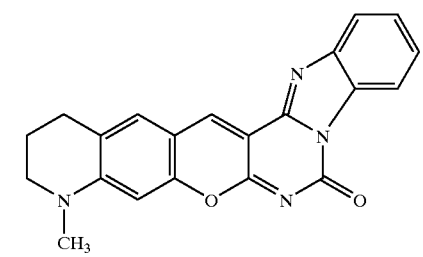
2
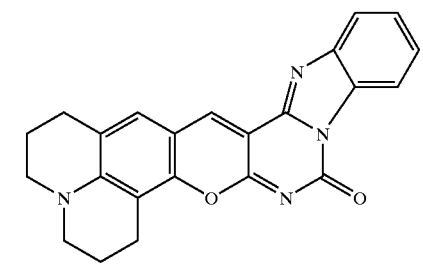
3
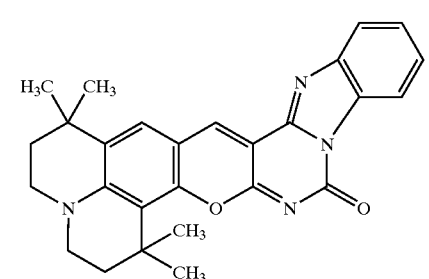
4
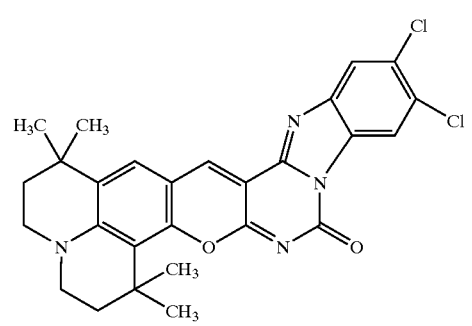
5
-continued
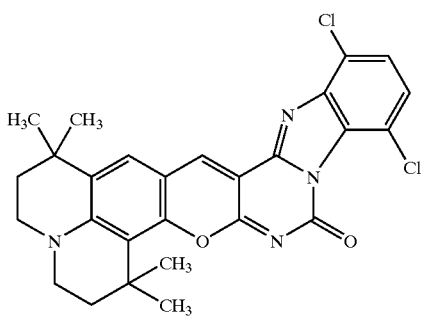
6
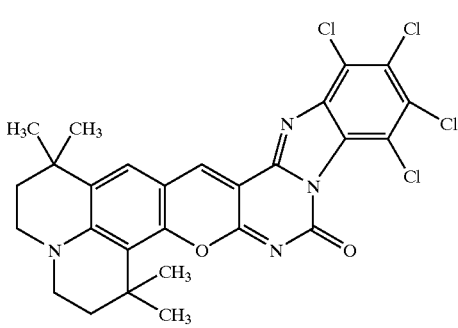
7
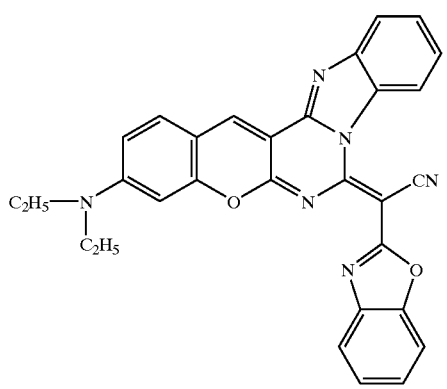
8
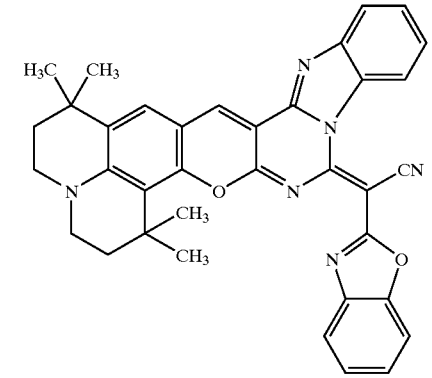
9

-continued
10
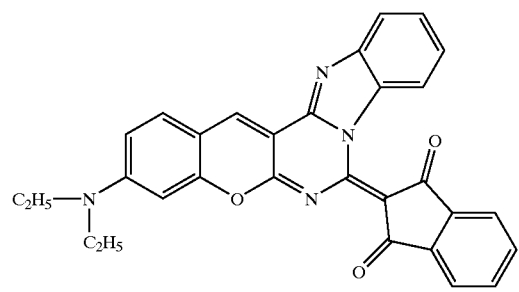
11
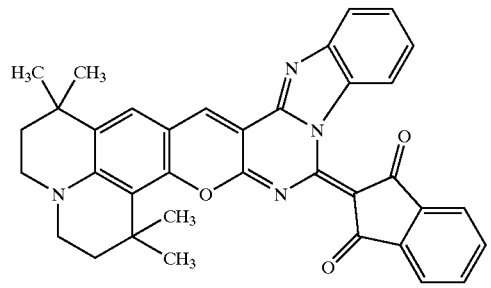
12
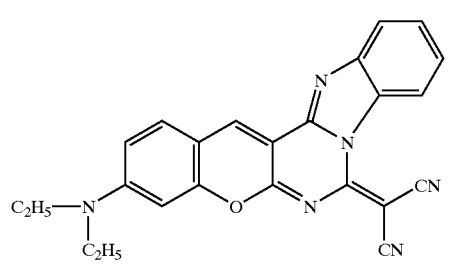
13
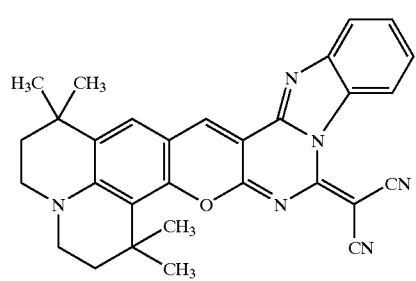
14
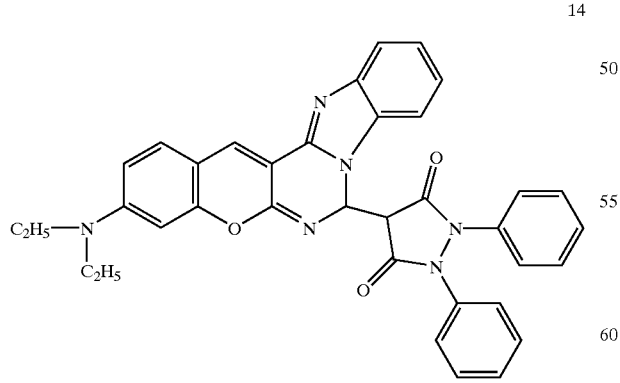
-continued
15
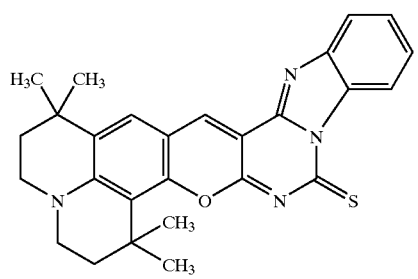
16
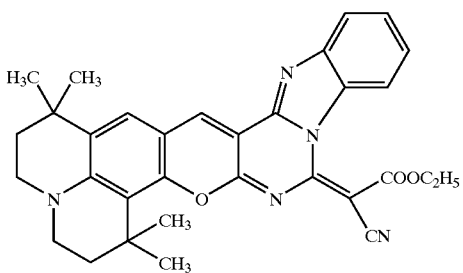
17
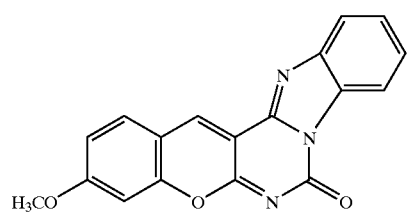
18
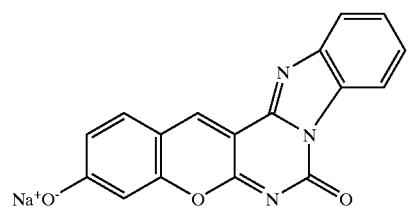
19
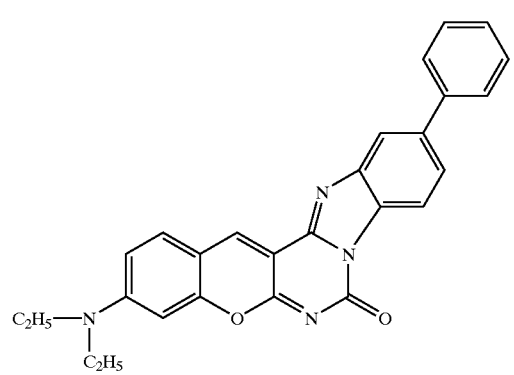

20
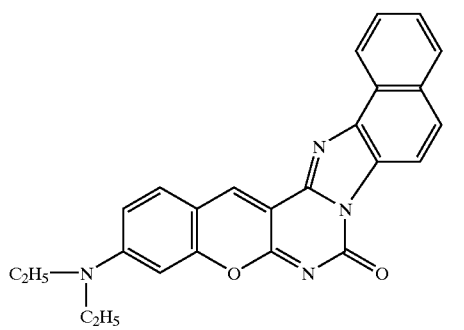
21
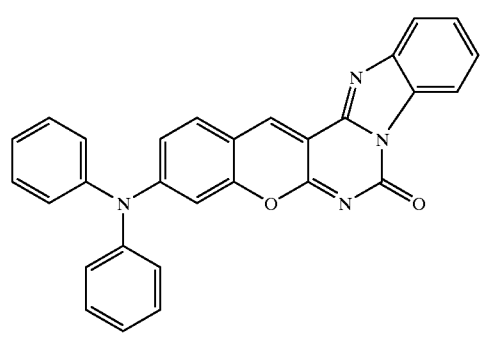
22
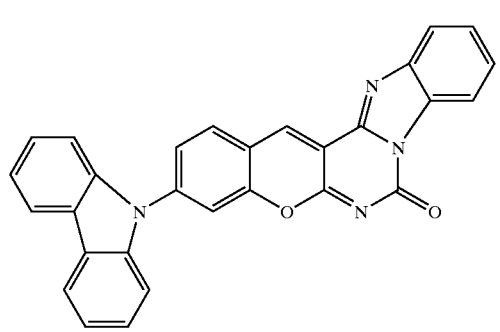
23
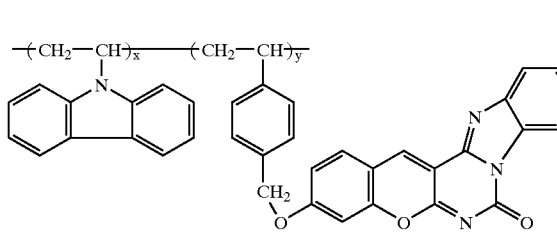
Weight average molecular weight: 11,000
x/y = 98/2 (by weight)
24
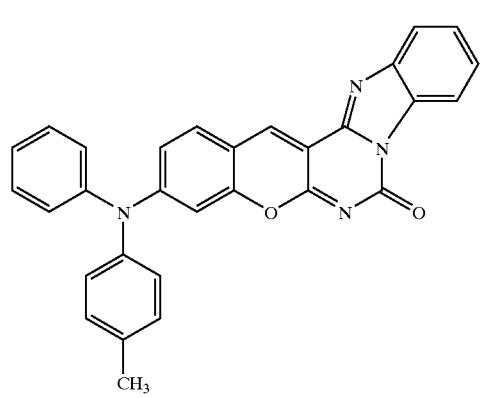
25
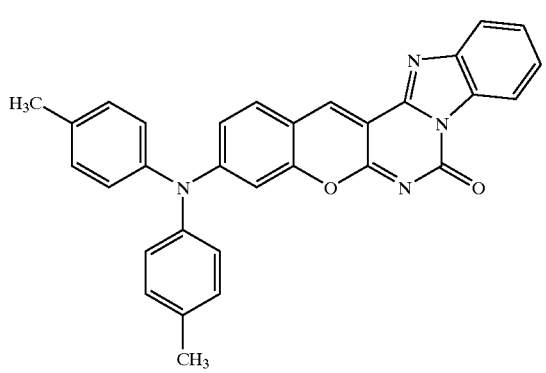
26
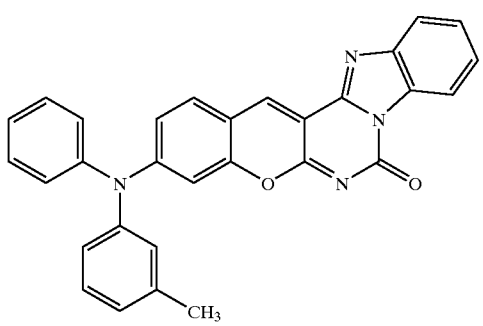
27
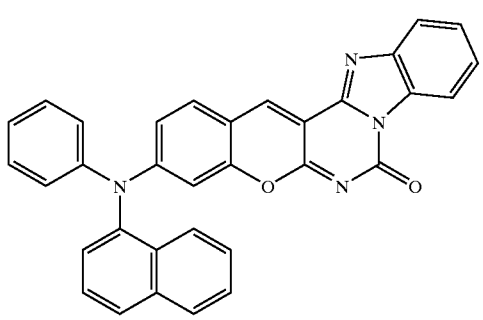
28
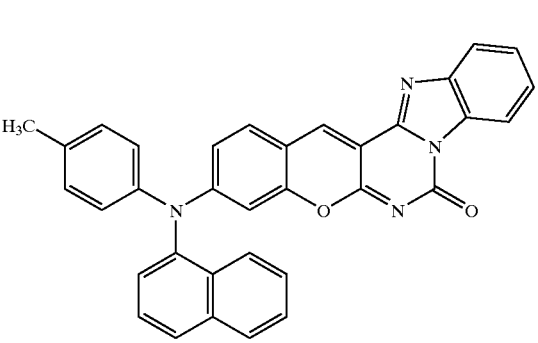
29
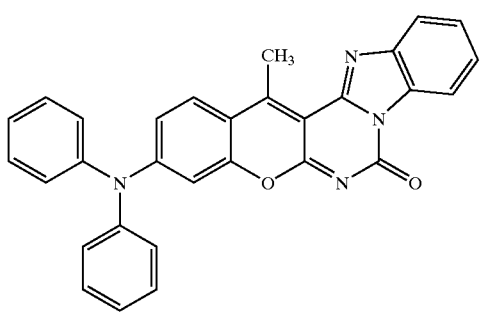

-continued
30
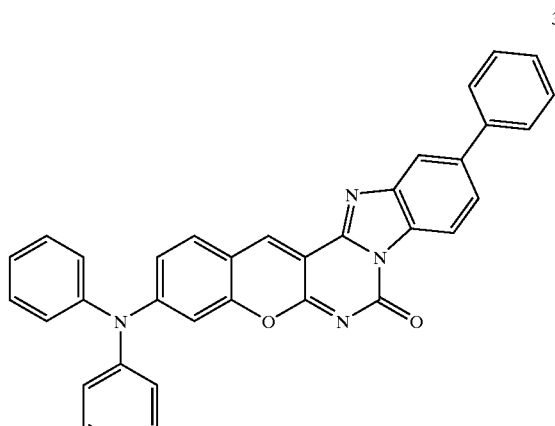
31
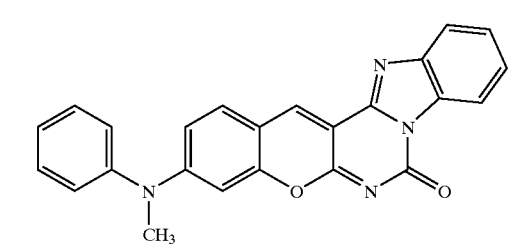
32
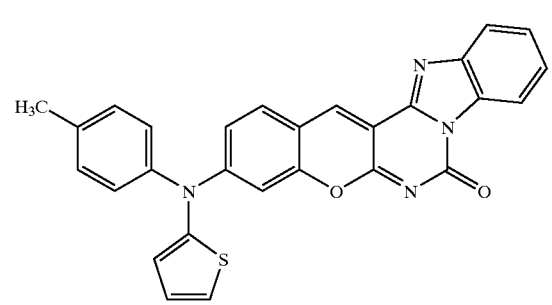
33
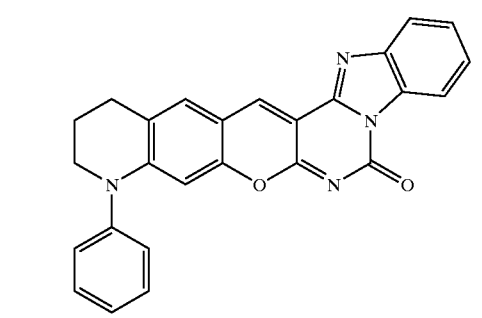
34
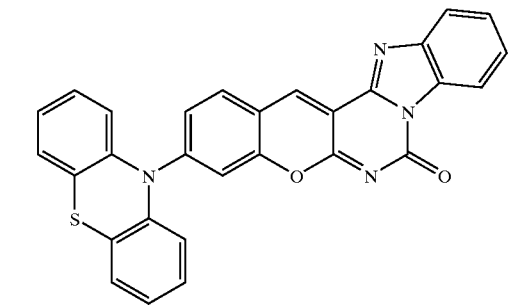
-continued
35
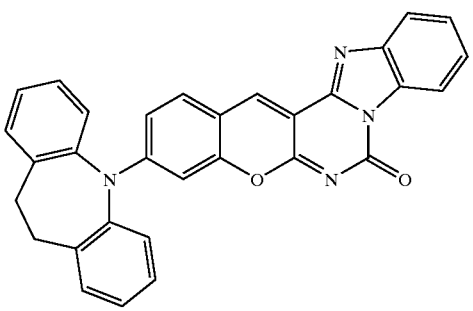
36
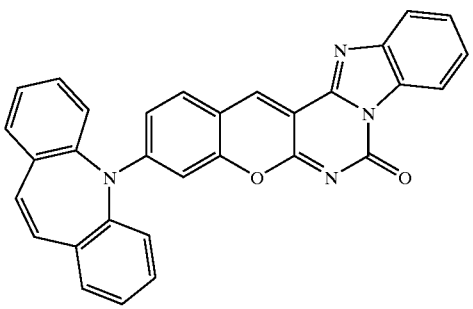
37
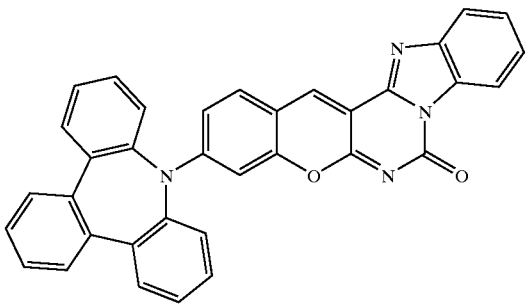
Specific examples of the compounds represented by formula (III) are shown below but the present invention is not limited thereto.
A-1
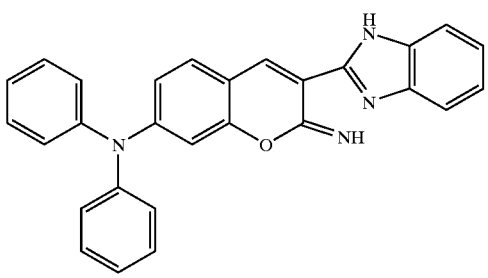

A-2
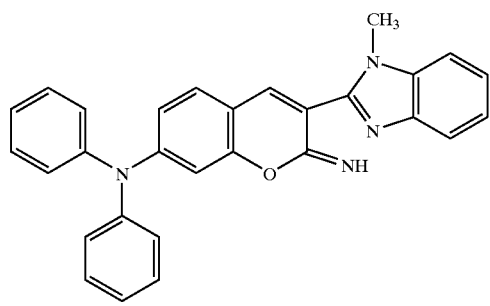
A-3
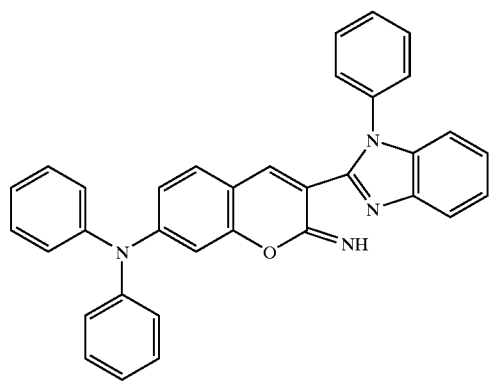
A-4
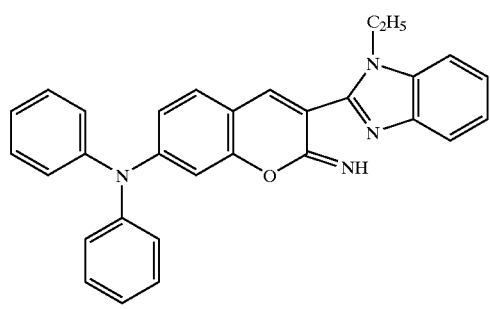
A-5
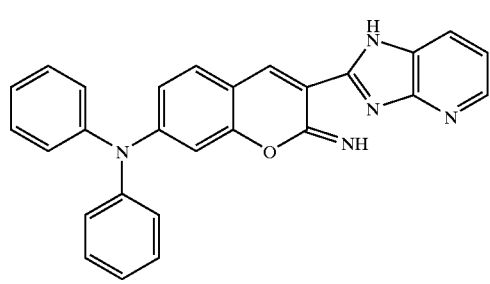
A-6
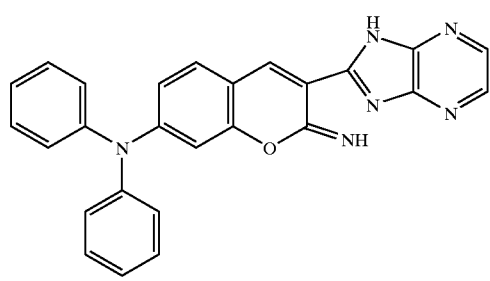
A-7
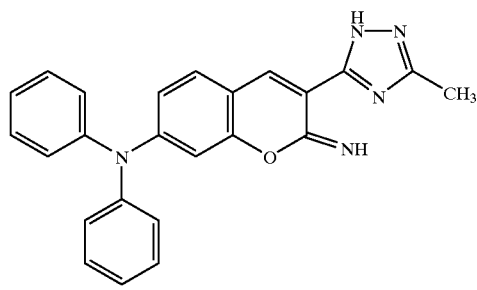
A-8
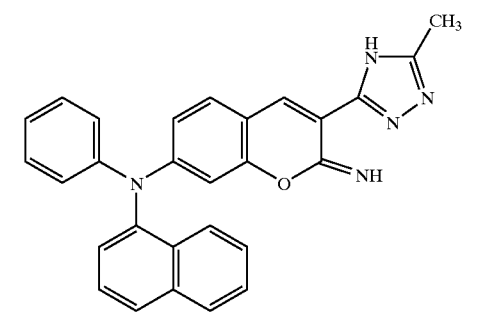
A-9
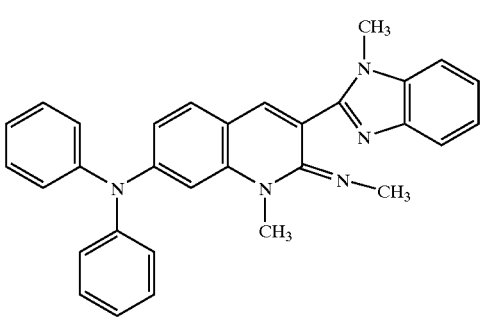
A-10
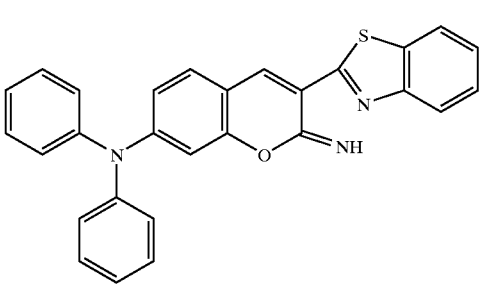
A-11
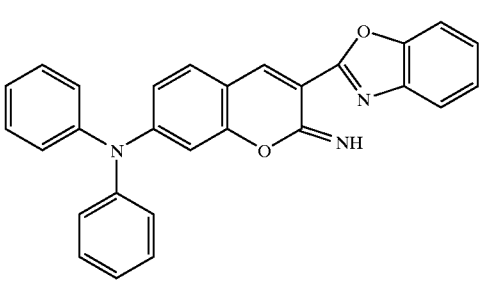

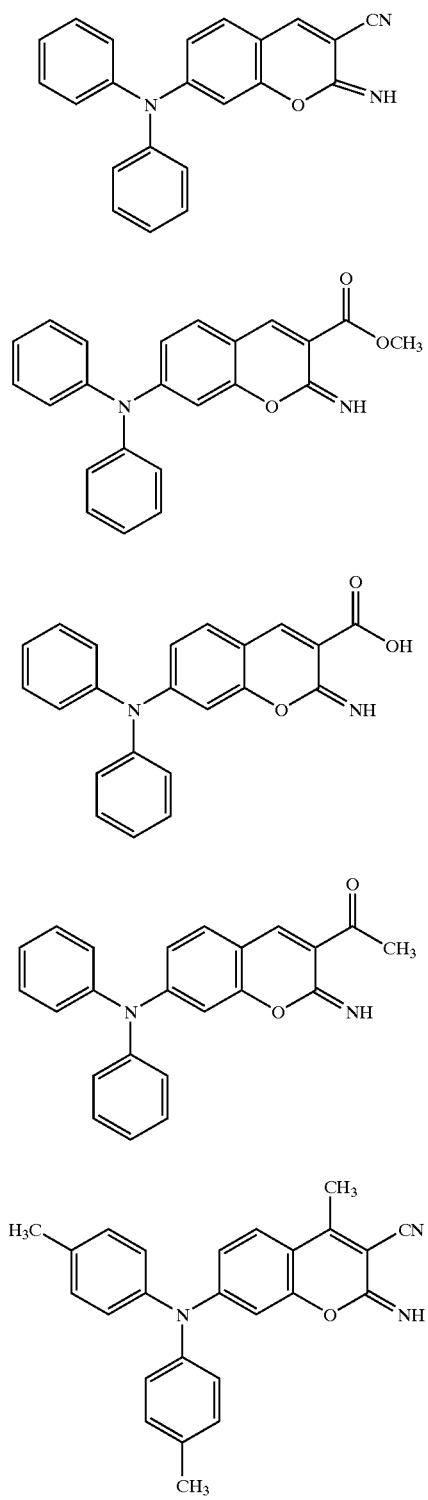
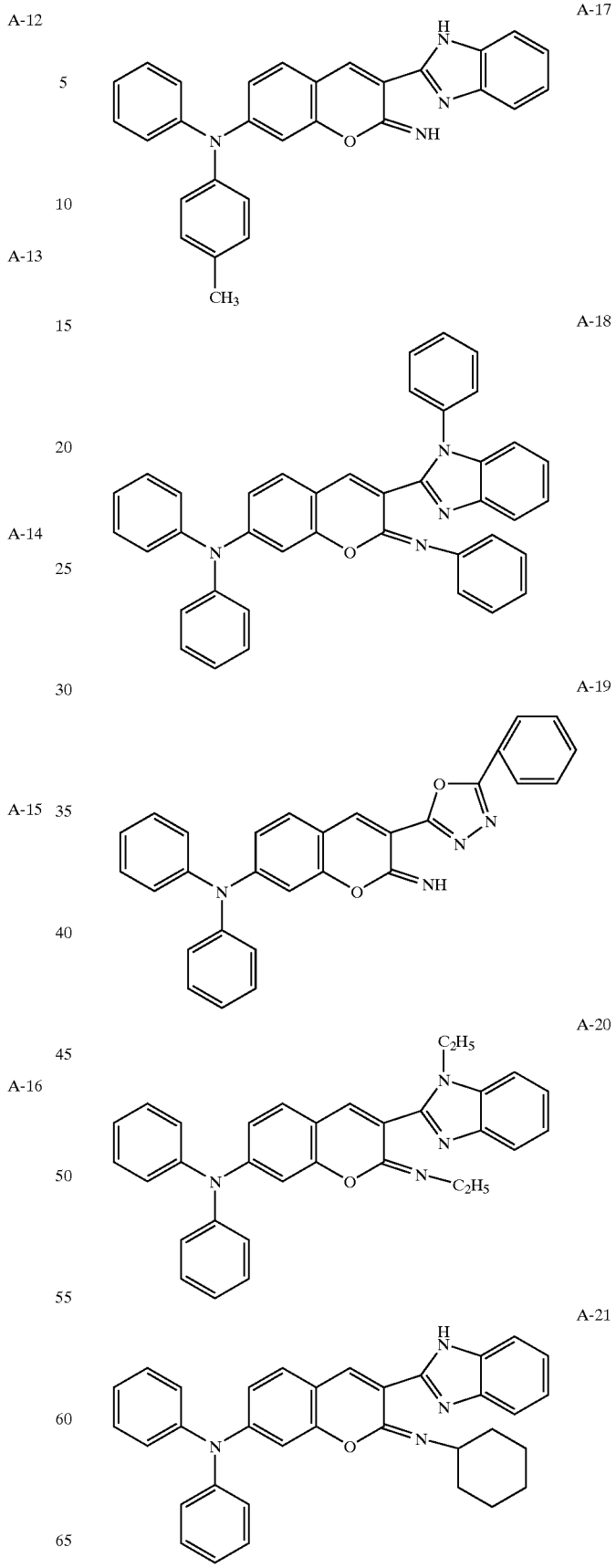

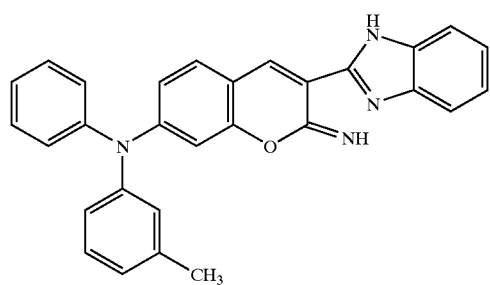
A-22
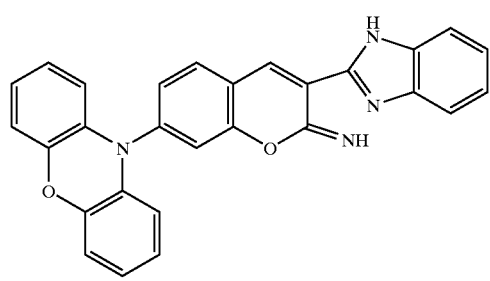
A-23
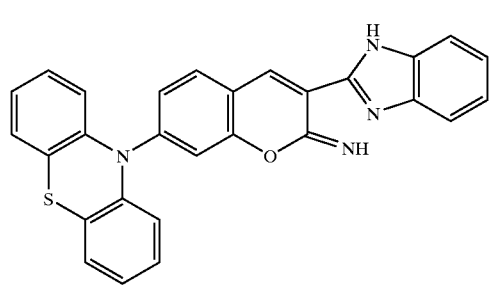
A-24
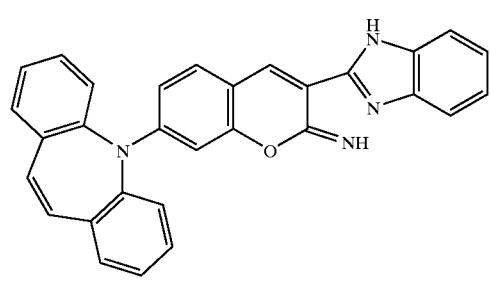
A-25
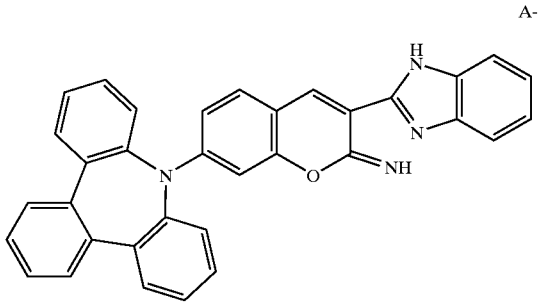
A-26
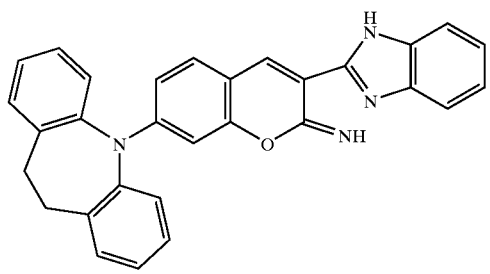
A-27
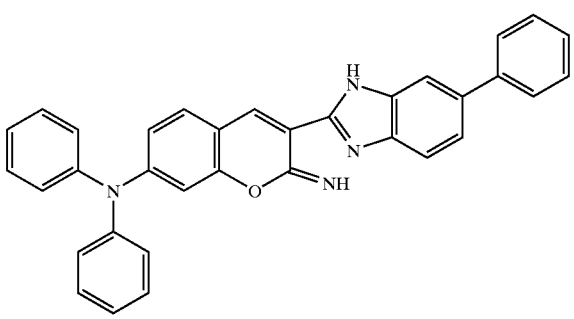
A-28
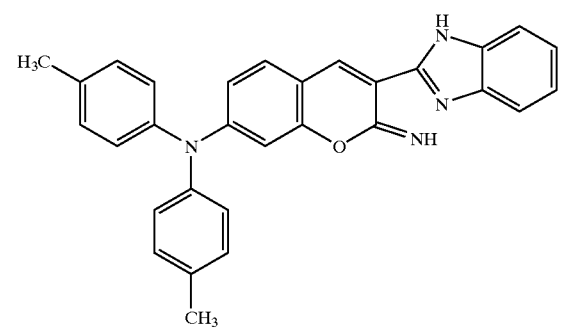
A-29
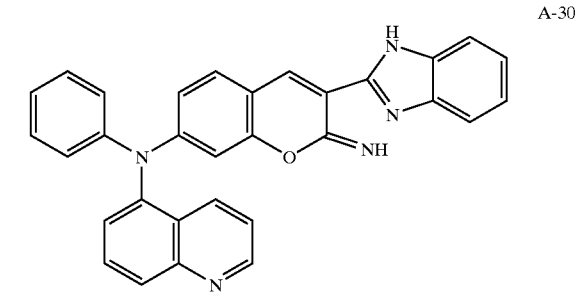
A-30
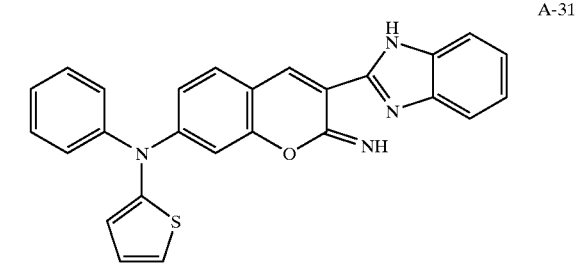
A-31

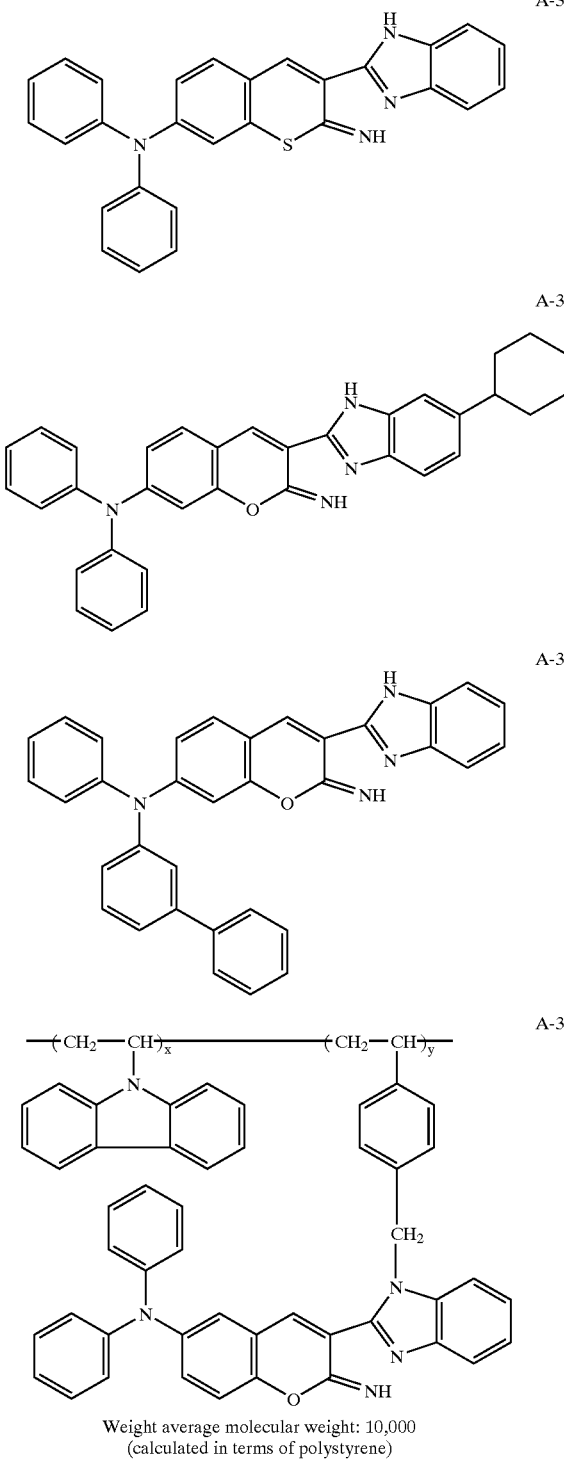

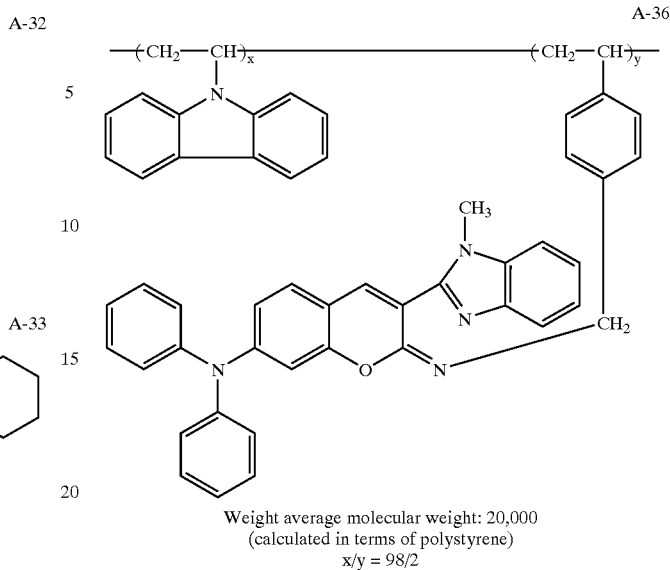

Weight average molecular weight: 20,000
(calculated in terms of polystyrene)
x/y = 98/2

The above compounds may be tautomers thereof.

The compound represented by formula (I') according to the present invention is described in detail below.

In formula (I'), $R_1'$, $R_2'$, $R_3'$, $R_4'$, $R_5'$, $R_6'$, $R_7'$, $R_8'$ and $R_1'$ each represents a hydrogen atom or a substituent. The substituent represented by $R_1'$, $R_2'$, $R_3'$, $R_4'$, $R_5'$, $R_6'$, $R_7'$, $R_8'$ and $R_{11}'$ has the same meaning as the substituent represented by $R_1$ to $R_8$ in formula (I).

$R_1'$, $R_2'$ and $R_3'$ each preferably represents a hydrogen atom or an alkyl group, more preferably a hydrogen atom or a lower alkyl group, and particularly preferably a hydrogen atom.

$R_4'$ preferably represents a hydrogen atom or an alkyl group, more preferably a hydrogen atom or a lower alkyl group, and particularly preferably a hydrogen atom or a methyl group.

$R_5'$, $R_6'$, $R_7'$ and $R_8'$ each preferably represents a hydrogen atom, an alkyl group, an aryl group, a halogen atom, a cyano group, a sulfonyl group, a heterocyclic group, or a benzene ring formed by the linkage of substituents, more preferably a hydrogen atom, a lower alkyl group (e.g., methyl, ethyl, n-propyl, isopropyl, t-butyl, trifluoromethyl), an aryl group (e.g., phenyl, p-methylphenyl, naphthyl), a halogen atom, or a cyano group, and still more preferably a hydrogen atom, a chlorine atom or a cyano group.

$R_{11}'$ preferably represents a hydrogen atom, an alkyl group, an aryl group, or a heterocyclic group, more preferably a hydrogen atom, a lower alkyl group, an aryl group, or an aromatic heterocyclic group, still more preferably a hydrogen atom, a methyl group, an ethyl group, or an aryl group having from 6 to 12 carbon atoms, and particularly preferably a hydrogen atom, a methyl group, or a phenyl group.

X' represents O, S or N—R' (wherein R' represents a hydrogen atom, an aliphatic hydrocarbon group, an aryl group or a heterocyclic group), and thus has the same meaning as X in formula (I). A preferred scope of X' is also the same as X in formula (I).

Z' represents a group represented by —NR$_a$' (R$_b$') or —OM', R$_a$' and R$_b$', which may be the same or different, each represents a hydrogen atom, an aliphatic hydrocarbon group, an aryl group or a heterocyclic group. Thus, Z' has the same meaning as Z in formula (I) and a preferred scope of Z' is also the same.

The compound represented by formula (I') is preferably represented by formula (I'-a):

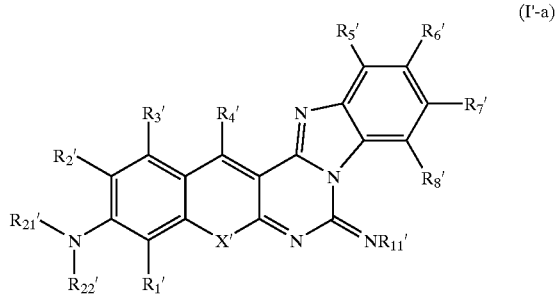

(I'-a)

wherein $R_1'$, $R_2'$, $R_3'$, $R_4'$, $R_5'$, $R_6'$, $R_7'$, $R_8'$, $R_{11}'$ and X' have the same meaning as those in formula (I') respectively, and the respective preferred scopes are also the same. $R_{21}'$ and $R_{22}'$ each represents an aryl group or a heterocyclic group. The aryl group is preferably a monocyclic or bicyclic aryl group having from 6 to 30 carbon atoms, more preferably a phenyl group having from 6 to 20 carbon atoms, and still more preferably a phenyl group having from 6 to 12 carbon atoms. The heterocyclic group is preferably an aromatic heterocyclic group. $R_{21}'$ and $R_{22}'$ each more preferably represents a monocyclic or bicyclic aryl group having from 6 to 30 carbon atoms, still more preferably a phenyl group having from 6 to 20 carbon atoms, and particularly preferably a phenyl group having from 6 to 12 carbon atoms.

The compound represented by formula (I') is preferably represented by formula (I'-b):

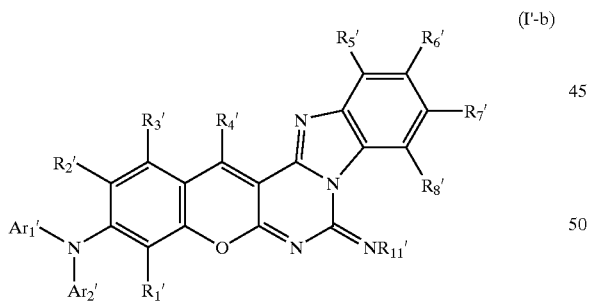

(I'-b)

wherein $R_1'$, $R_2'$, $R_3'$, $R_4'$, $R_5'$, $R_6'$, $R_7'$, $R_8'$ and $R_{11}'$ have the same meaning as those in formula (I') respectively, and the respective preferred scopes are also the same. $Ar_1'$ and $Ar_{21}'$ each represents an aryl group or an aromatic heterocyclic group. The aryl group is preferably a monocyclic or bicyclic aryl group having from 6 to 30 carbon atoms, more preferably a phenyl group having from 6 to 20 carbon atoms, and still more preferably a phenyl group having from 6 to 12 carbon atoms. $Ar_1'$ and $Ar_2'$ each more preferably represents a monocyclic or bicyclic aryl group having from 6 to 30 carbon atoms, still more preferably a phenyl group having from 6 to 20 carbon atoms, and particularly preferably a phenyl group having from 6 to 12 carbon atoms.

The compounds represented by formula (I') may be low molecular weight compounds, or may be high molecular weight compounds having the residue bonding to the polymer main chain (preferably having a weight average molecular weight of from 1,000 to 5,000,000, more preferably from 5,000 to 2,000,000, and still more preferably from 10,000 to 1,000,000), or may be high molecular weight compounds having the compounds according to the present invention at the main chain (preferably having a weight average molecular weight of from 1,000 to 5,000,000, more preferably from 5,000 to 2,000,000, and still more preferably from 10,000 to 1,000,000). The high molecular weight compounds may be homopolymers or copolymers with other polymers, and the copolymers may be random copolymers or block copolymers. The compounds for use in the present invention are preferably low molecular weight compounds. Further, the above formula takes limiting structure for convenience sake but the compounds may be tautomers thereof.

Specific examples of the compounds represented by formula (I') are shown below but the present invention is not limited thereto.

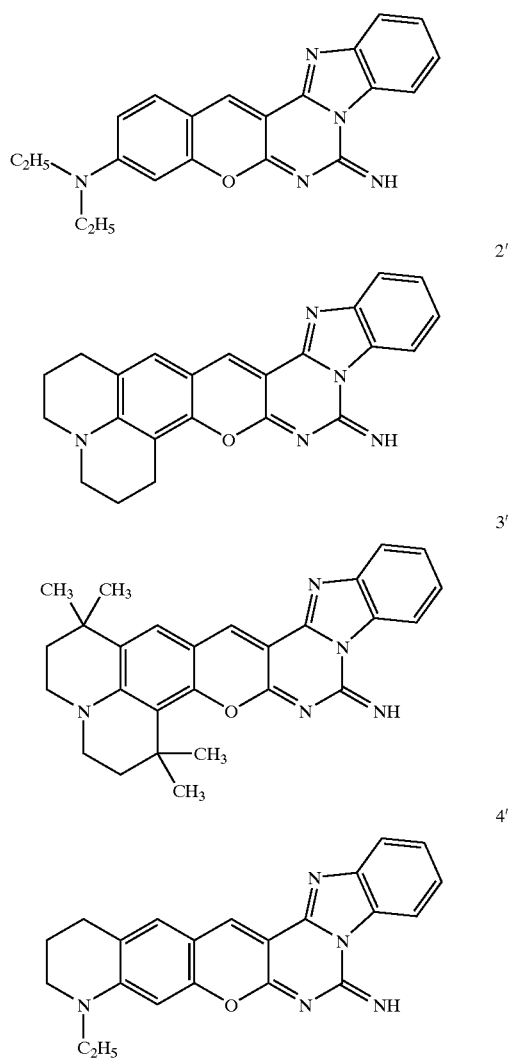

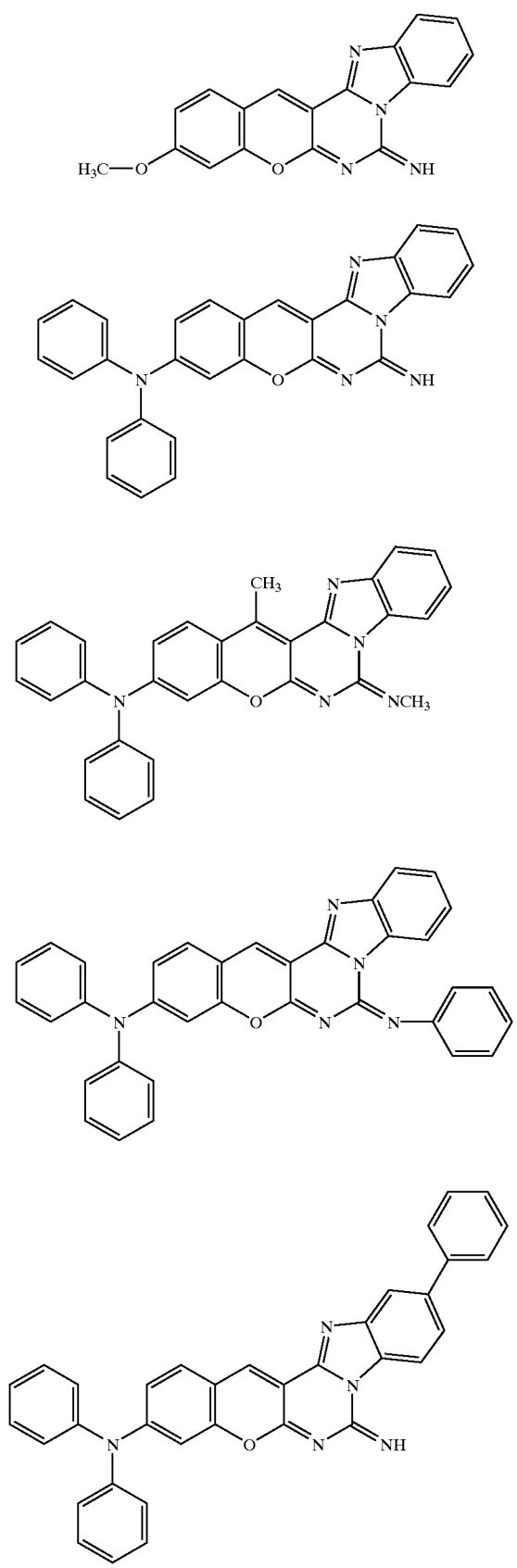
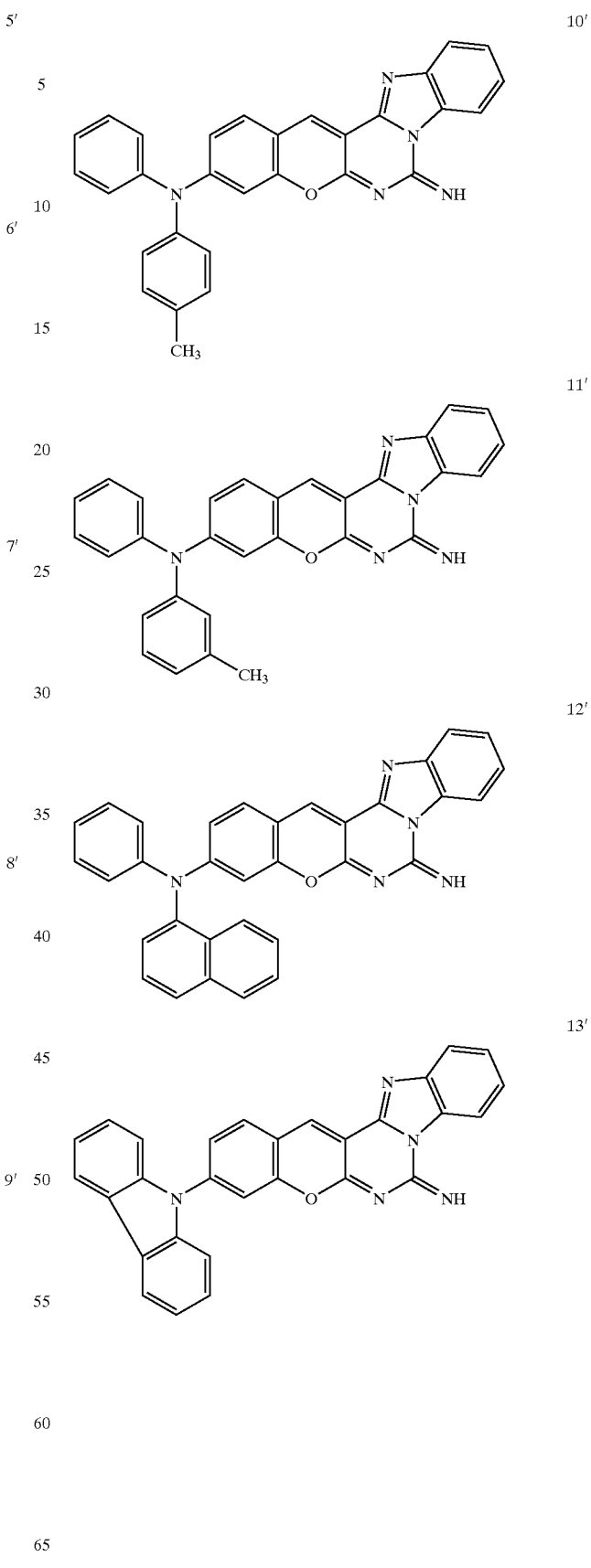

14'
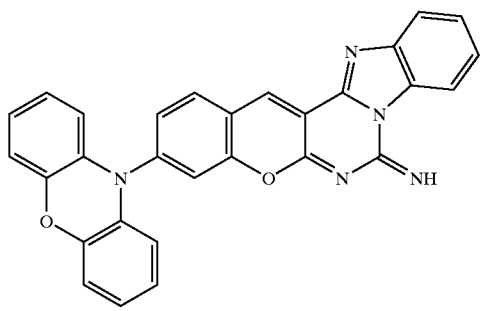
15'
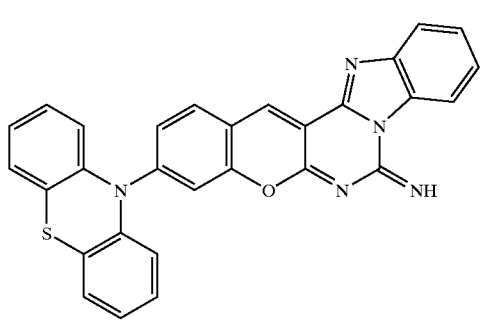
16'
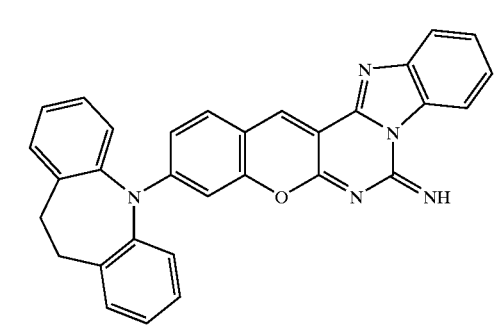
17'
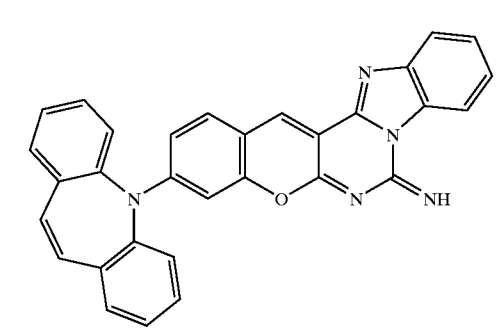
18'
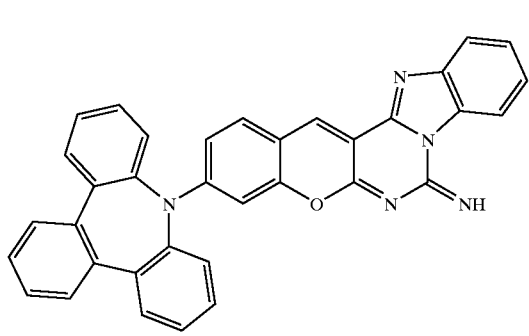
19'
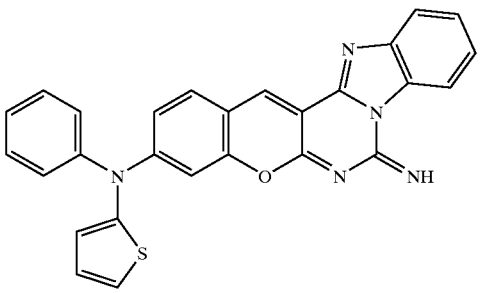
20'
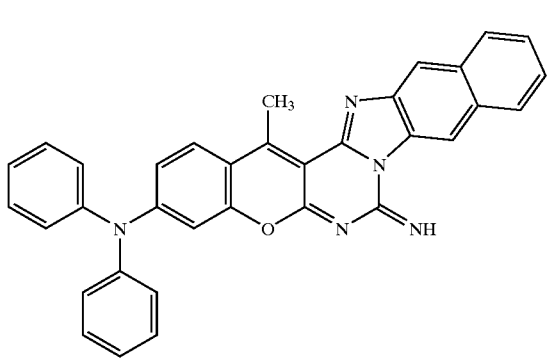
21'
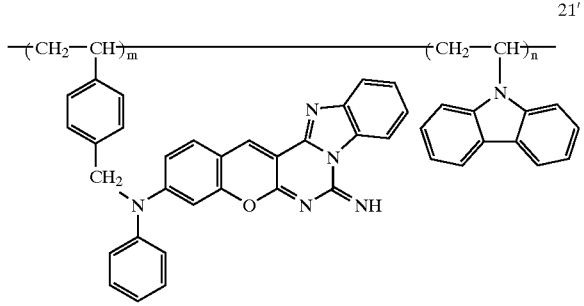
Weight average molecular weight: 20,000
(calculated in terms of polystyrene)
m/n = 2/98 (by weight)

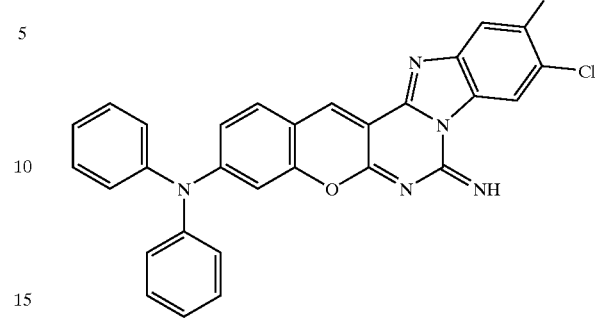
25'
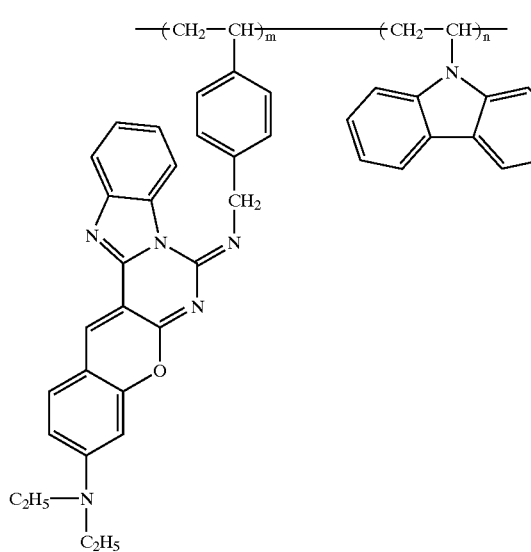
22'
Weight average molecular weight: 30,000
(calculated in terms of polystyrene)
m/n = 2/98 (by weight)
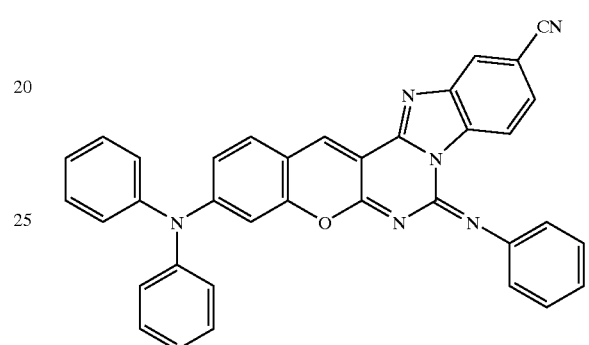
26'
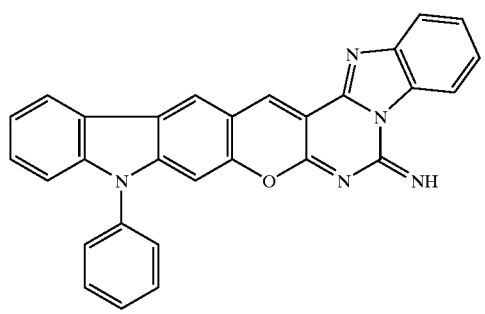
23'
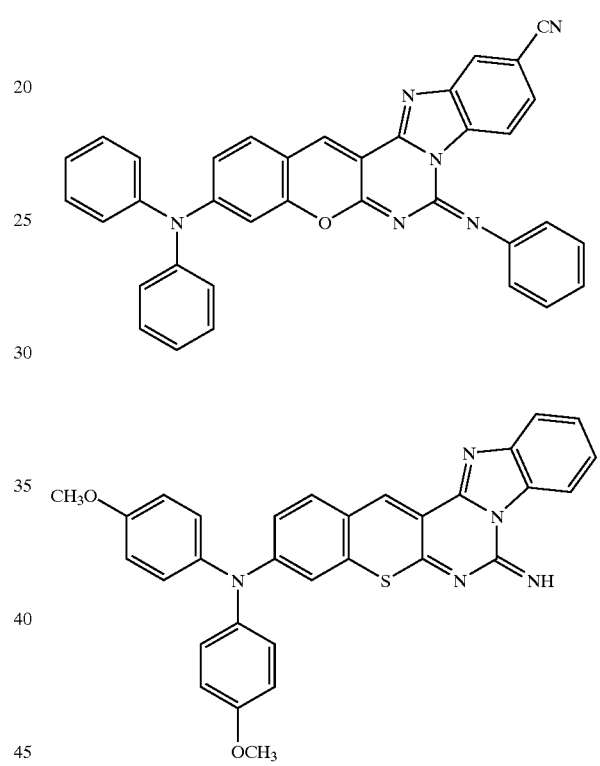
27'
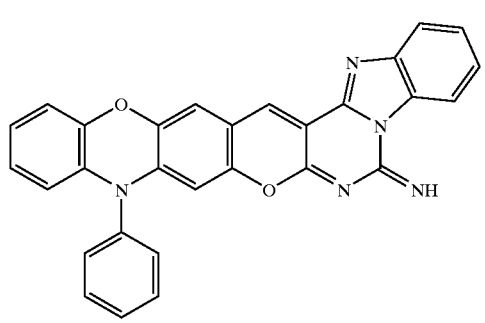
24'
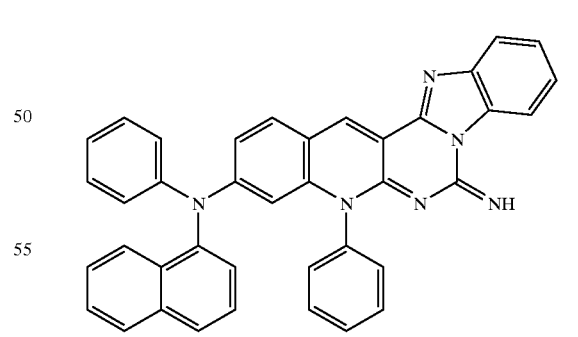
28'
The above compounds may be tautomers thereof.
A synthesis method of a compound represented by formula (I) according to the present invention is described below. A representative synthesis method is shown in Reaction Scheme 1.

Reaction Scheme 1

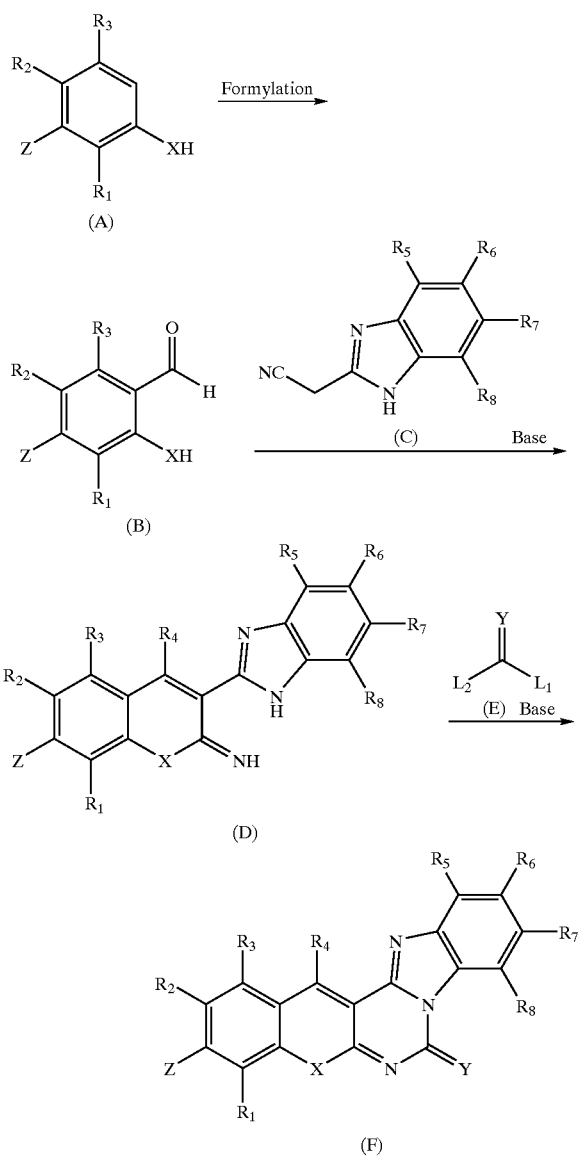

wherein $R_1$, $R_2$, $R_3$, $R_4$, $R_5$, $R_6$, $R_7$, $R_8$, X, Y and Z have the same meaning as those in formula (I) respectively. $L_1$ and $L_2$ each represents a separating group, e.g., a halogen atom, an alkoxyl group or an azole group.

The synthesis of Compound (A) to Compound (B) in Reaction Scheme 1 is a formylation reaction to a phenyl group and the synthesis can be performed, for example, according to the method described in *Shin Jikken Kagaku Koza* 14, pp. 683 to 705, Maruzen Co., Ltd. Specifically, there is Vilsmeier reaction which uses dimethylformamide (preferably in an amount of from 1 to 100 equivalent amount, more preferably from 1 to 50 equivalent amount, based on the amount of Compound (A)) and phosphorus oxychloride (preferably in an amount of from 1 to 5 equivalent amount, more preferably from 1 to 2 equivalent amount, based on the amount of Compound (A)). The synthesis of Compound (B) to Compound (D) is a synthesis method based on the cyclization in the presence of a base (preferably organic bases, more preferably organic amines, e.g., piperidine, preferably in an amount of from 0.001 to 10 equivalent amount, more preferably from 0.01 to 2 equivalent amount, and still more preferably from 0.1 to 2 equivalent amount, based on the amount of Compound (B)), wherein as a solvent, hydrocarbons (e.g., benzene, toluene, xylene), nitriles (e.g., acetonitrile), alcohols (e.g., methanol, ethanol, isopropanol, butanol), ethers (e.g., tetrahydrofuran, 1,4-dioxane, diethyl ether), and amides (e.g., dimethylformamide, dimethylacetamide) are preferably used, and the reaction temperature is preferably from 0 to 150° C., more preferably from 15 to 120° C. The synthesis of Compound (D) to Compound (F) is a synthesis method based on the cyclization using Compound (D), Compound (E) having two separating groups (e.g., phosgene, triphosgene, ethyl ortho-formate, phenyl orthoformate, carbonyl diimidazole, phenyl chlorothioformate, preferably in an amount of from 1 to 10 equivalent amount, more preferably from 1 to 5 equivalent amount, and still more preferably from 1 to 2 equivalent amount, based on the amount of Compound (D)), and a base (preferably organic amines, more preferably azoles or tertiary amines, specifically pyridine, triethylamine, preferably in an amount of from 1 to 100 equivalent amount, more preferably from 1 to 50 equivalent amount, based on the amount of Compound (D)), wherein as a solvent, organic halides (e.g., chloroform, dichloroethane, dichloromethane), benzene, toluene, xylene, acetonitrile, alcohols (e.g., methanol, ethanol, isopropanol, butanol), pyridine, and lutidine are preferably used, more preferably pyridine and lutidine, and the reaction temperature is preferably from 0 to 150° C., more preferably from 15 to 120° C.

A synthesis method of a compound represented by formula (III) according to the present invention is described below. A representative synthesis method is shown in Reaction Scheme 2.

Reaction Scheme 2

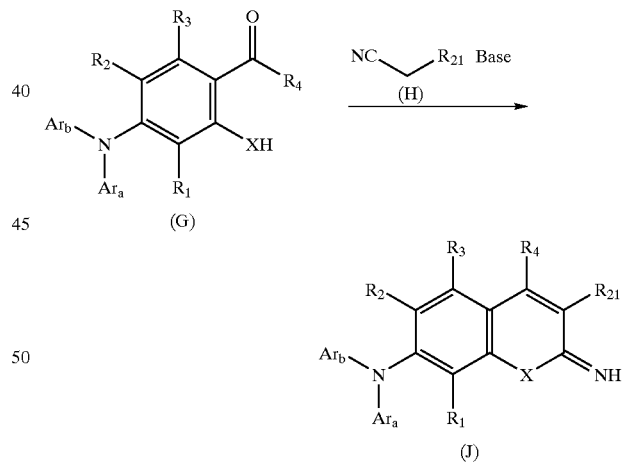

wherein $R_1$, $R_2$, $R_3$, $R_4$, $R_{21}$, $Ar_a$, $Ar_b$ and X have the same meaning as those in formula (III) respectively.

The synthesis of Compound (G) to Compound (J) is a synthesis method based on the cyclization in the presence of a base (preferably organic bases, more preferably organic amines, e.g., piperidine, preferably in an amount of from 0.001 to 10 equivalent amount, more preferably from 0.01 to 2 equivalent amount, and still more preferably from 0.1 to 2 equivalent amount, based on the amount of Compound (G)), wherein as a solvent, hydrocarbons (e.g., benzene, toluene, xylene), nitrites (e.g., acetonitrile), alcohols (e.g., methanol, ethanol, isopropanol, butanol), ethers (e.g., tetrahydrofuran, 1,4-dioxane, diethyl ether), and amides (e.g., dimethylformamide, dimethylacetamide) are preferably used, and the reaction temperature is preferably from 0 to 150° C., more preferably from 15 to 120° C.

The luminous device according to the present invention comprises a pair of electrodes, which are an anode and a cathode, having formed therebetween a luminous layer or a plurality of organic compound thin layers including a luminous layer. The organic compound thin layers may further comprise a positive hole-injecting layer, a positive hole-transporting layer, an electron-injecting layer, an electron-transporting layer, a protecting layer, etc., in addition to a luminous layer. Each of these layers may have different functions. Various materials can be used to form each layer.

The anode is to supply positive holes to a positive hole-injecting layer, a positive hole-transporting layer, a luminous layer, etc., and metals, alloys, metal oxides, electrically conductive compounds, or mixtures of these compounds can be used therefor, and materials having a work function of 4 eV or more are preferably used. Specific examples of the materials include electrically conductive metal oxides such as a tin oxide, a zinc oxide, an indium oxide, an indium tin oxide (ITO), etc., metals such as gold, silver, chromium, nickel, etc., mixtures or laminations of these metals with electrically conductive metal oxides, inorganic electrically conductive materials such as copper iodide, copper sulfide, etc., organic electrically conductive materials such as polyaniline, polythiophene, polypyrrole, etc., and laminations of these materials with ITO. Electrically conductive metal oxides are preferably used, and ITO is particularly preferably used in view of producibility, high conductivity and transparency. The film thickness of the anode can be selected arbitrarily according to materials used but is generally preferably from 10 nm to 5 µm, more preferably from 50 nm to 1 µm, and still more preferably from 100 nm to 500 nm.

The anode generally comprises lamination formed on a soda-lime glass, non-alkali glass or transparent resin substrate. When a glass substrate is used, non-alkali glass is preferably used for lessening elution of ions from the glass. Further, when soda-lime glass is used, it is preferred to provide a barrier coat such as silica. The thickness of the substrate is not particularly limited so long as it can sufficiently stand the mechanical strength. When glass is used, the thickness is generally 0.2 mm or more, preferably 0.7 mm or more.

Various processes are used in manufacturing the anode according to the materials to be used. In the case of using ITO, for example, thin layers are formed by an electron beam process, a sputtering process, a resistance heating deposition process, a chemical reaction process (a sol-gel process), or the process of coating the dispersion of an indium tin oxide.

It is possible to reduce the driving voltage or increase the luminous efficiency of the device by the process such as washing of the anode. In the case of using ITO, for example, UV-ozone processing is effective.

The cathode is to supply electrons to an electron-injecting layer, an electron-transporting layer, a luminous layer, etc., and the cathode is selected taking into consideration the adhesion with the adjacent electron-injecting layer, electron-transporting layer, luminous layer, etc., ionization potential and stability. As materials of the cathode, metals, alloys, metal oxides, electrically conductive compounds, or mixtures of these compounds can be used. Specific examples include alkali metals (e.g., Li, Na, K) or fluorides of them, alkaline earth metals (e.g., Mg, Ca) or fluorides of them, gold, silver, lead, aluminum, sodium-potassium alloys or mixed metals of them, lithium-aluminum alloys or mixed metals of them, magnesium-silver alloys or mixed metals of them, and rare earth metals such as indium, ytterbium, etc., preferably materials having a work function of 4 eV or less, and more preferably aluminum, lithium-aluminum alloys or mixed metals of them, and magnesium-silver alloys or mixed metals of them. The film thickness of the cathode can be selected arbitrarily according to materials used but is generally preferably from 10 nm to 5 µm, more preferably from 50 nm to 1 µm, and still more preferably from 100 nm to 1 µm.

Processes such as an electron beam process, a sputtering process, a resistance heating deposition process, and a coating process are used in the manufacture of the cathode, and a single metal can be vapor deposited or two or more components can be deposited at the same time. Further, a plurality of metals can be deposited at the same time to form an alloy electrode, alternatively a previously prepared alloy can be deposited.

It is preferred that the sheet resistance of the anode and the cathode be low, preferably several hundred Ω/square or less.

The luminous layer may be made of any material so long as, when electric field is impressed, the luminous layer formed does not prevent positive holes from being injected from the anode, the positive hole-injecting layer and the positive hole-transporting layer, electrons from being injected from the cathode, the electron-injecting layer and the electron-transporting layer, and offers the functions of transferring the electric charge injected and recombining the electrons and positive holes to effect emission. Preferably the luminous layer contains the compound according to the present invention but luminous materials other than the compound according to the present invention can also be used, and as such materials, e.g., benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perynone derivatives, oxadiazole derivatives, aldazine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, aromatic dimethylidyne compounds, various metal complexes represented by metal complexes of 8-quinolinol derivatives and rare earth metal complexes, and polymer compounds such as polythiophene, polyphenylene, and polyphenylenevinylene are exemplified. The film thickness of the luminous layer is not particularly restricted but it is generally preferably from 1 nm to 5 µm, more preferably from 5 nm to 1 µm, and still more preferably from 10 nm to 500 nm.

The luminous layer can be formed by any process, e.g., a resistance heating deposition process, an electron beam process, a sputtering process, a molecular lamination process, a coating process (a spin coating process, a cast coating process, a dip coating process), or an LB process is used, preferably a resistance heating deposition process and a. coating process.

Materials of the positive hole-injecting layer and the positive hole-transporting layer are sufficient if they have any of the functions of injecting positive holes from the anode, transporting positive holes, and barriering off the electrons injected from the cathode. Specific examples of the materials include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne-based compounds, porphyrin-based compounds, polysilane-based compounds, poly(N-vinylcarbazole) derivatives, aniline-based copolymers, and electrically conductive high molecular weight oligomers such as tihophene oligomers and polythiophene. The film thickness of the positive hole-injecting layer and the positive hole-transporting layer is not particularly limited but it is generally preferably from 1 nm to 5 µm, more preferably from 5 nm to 1 µm, and still more preferably from 10 nm to 500 nm. The positive hole-injecting layer and the positive hole-transporting layer may be single layer structure comprising one or two or more of the above materials, or may be multilayer structure comprising a plurality of layers of the same composition or different compositions.

The positive hole-injecting layer and the positive hole-transporting layer are formed by a vacuum deposition process, an LB process, or the process of dissolving or dispersing the above-described positive hole-injecting and transporting agent in a solvent and coating (a spin coating process, a cast coating process, a dip coating process). In the case a coating process, a positive hole-injecting and transporting agent can be dissolved or dispersed with a resin component. Examples of such resin components include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, vinyl acetate, ABS resin, polyurethane, melamine resin, unsaturated polyester resin, alkyd resin, epoxy resin, silicone resin, etc.

Materials of the electron-injecting layer and the electron-transporting layer are sufficient if they have any of the functions of injecting electrons from the cathode, transporting electrons, and barriering off the positive holes injected from the anode. Specific examples of the materials include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodiimide derivatives, fluorenylidene methane derivatives, distyrylpyrazine derivatives, heterocyclic tetracarboxylic anhydride such as naphthalene and perylene, phthalocyanine derivatives, and various metal complexes represented by metal complexes such as metal complexes of 8-quinolinol derivatives and metal complexes having a ligand such as metal phthalocyanine, benzoxazole or benzothiazole. The film thickness of the electron-injecting layer and the electron-transporting layer is not particularly restricted but it is generally preferably from 1 nm to 5 µm, more preferably from 5 nm to 1 µm, and still more preferably from 10 nm to 500 nm. The electron-injecting layer and the electron-transporting layer may be single layer structure comprising one or two or more of the above materials, or may be multilayer structure comprising a plurality of layers of the same composition or different compositions.

The electron-injecting layer and the electron-transporting layer are formed by a vacuum deposition process, an LB process, or the process of dissolving or dispersing the above-described electron-injecting and transporting agent in a solvent and coating (a spin coating process, a cast coating process, a dip coating process). In the case a coating process, an electron-injecting and transporting agent can be dissolved or dispersed with a resin component. As the resin components, those exemplified in the positive hole-injecting and transporting layers can be applied.

Materials of the protective layer are sufficient if they have the function of preventing substances which accelerates the deterioration of the device, such as water or oxygen, from entering the device. Specific examples of the materials include metals, e.g., In, Sn, Pb, Au, Cu, Ag, Al, Ti, Ni, etc., metal oxides, e.g., MgO, SiO, $SiO_2$, $Al_2O_3$, GeO, NiO, CaO, BaO, $Fe_2O_3$, $Y_2O_3$, $TiO_2$, etc., metal fluorides, e.g., $MgF_2$, LiF, $AlF_3$, $CaF_2$, etc., polyethylene, polypropylene, polymethyl methacrylate, polyimide, polyurea, polytetrafluoroethylene, polychlorotrifluoroethylene, polydichlorodifluoroethylene, copolymers of chlorotrifluoroethylene and dichlorodifluoroethylene, copolymers obtained by copolymerizing tetrafluoroethylene with monomer mixtures containing at least one comonomer, fluorine-containing copolymers having cyclic structure at the main chain of the copolymer, water-absorbing substances having a water absorption coefficient of 1% or more, and moisture-proof materials having a water absorption coefficient of 0.1% or less.

The forming process of the protective layer is also not particularly restricted and, e.g., a vacuum deposition process, a sputtering process, a reactive sputtering process, an MBE (molecular beam epitaxy) process, a cluster ion beam process, an ion-plating process, a plasma polymerization process (a high frequency exciting ion-plating process), a plasma CVD process, a laser CVD process, a heat CVD process, a gas source CVD process, or a coating process can be applied.

The present invention will be illustrated in greater detail with reference to the following Examples, but the invention should not be construed as being limited thereto.

EXAMPLE 1

Synthesis of Compound (1)

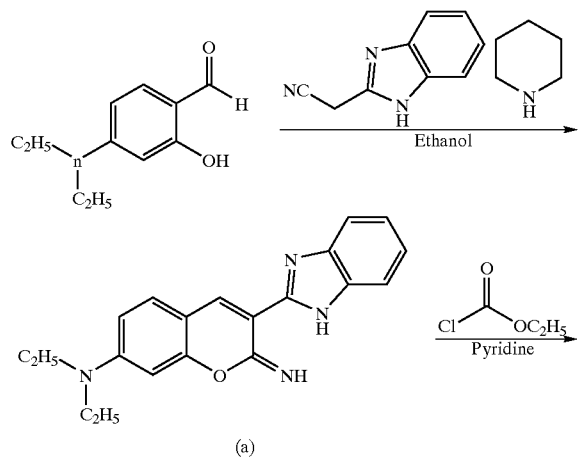

(a)

EXAMPLE 2

Synthesis of Compound (3)

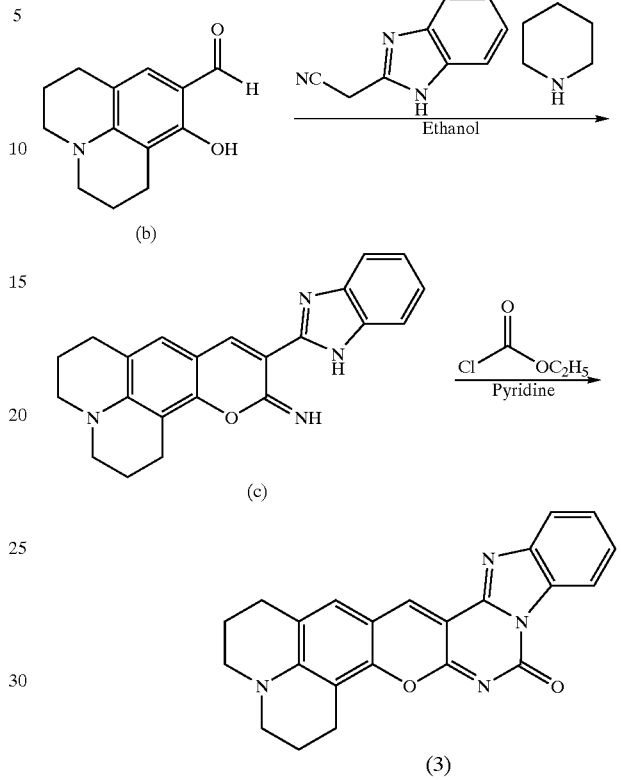

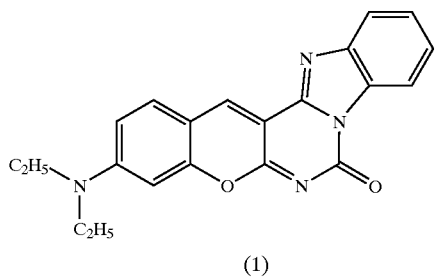

4-Diethylaminosalicylaldehyde (25.0 g), 20.2 g of 2-benzimidazolylacetonitrile, 500 ml of ethanol and 12.7 ml of piperidine were put in a reaction vessel and refluxed with heating for 7 hours. Thereafter, the temperature of the solution was lowered to room temperature, crystals precipitated were filtered out, washed with ethanol, and dried, thereby 39.1 g of Compound (a) was obtained (yield: 91%).

To 5.0 g of Compound (a) were added 500 ml of pyridine and 2 ml of triethylamine, and 2 ml of ethyl chloroformate was dropwise added thereto at room temperature under nitrogen atmosphere. After dropping was terminated, the reaction solution was refluxed with heating for 12 hours, and then the temperature of the solution was reduced to room temperature. The crystals precipitated were filtered out, washed with ethanol, and dried, thereby 3.1 g of Compound (1) was obtained (yield: 60%). The results of analysis of Compound (1) were as follows.

Absorption spectrum: Absorption maximum wavelength: 518 nm; (in a dichloroethane solvent); Fluorescence spectrum: Fluorescence maximum wavelength: 548 nm; (in a dichloroethane solvent); Elemental analysis ($C_{21}H_{18}O_2N_4$): Calculated value: C: 70.38%, H: 5.06%, N: 15.63%; Measured value: C: 70.77%, H: 5.04%, N: 15.79%.

In the same manner as in Example 1, 4.9 g of Compound (c) was obtained (yield: 69%) using 4.3 g of Compound (b) in place of 4-diethylaminosalicylaldehyde, 3.1 g of 2-benzimidazolyacetonitrile, 40 ml of ethanol and 2.0 ml of piperidine. Compound (3) (1.2 g) (yield: 57%) Was obtained using 2.0 g of Compound (C), 50 ml of pyridine, 0.8 ml of triethylamine, and 1 of ethyl chloroformate. The results of analysis of Compoud (3) were as follows.

Absorption spectrum: Absorption maximum wavelength: 536 nm; (in a dichloroethane solvent); Fluorescence spectrum: Fluorescence maximum wavelength: 557 nm; (in a dichloroethane solvent); Elemental analysis ($C_{23}H_{18}O_2N_4$): Calculated value: C: 72.24%, H: 4.74%, N: 14.65%; Measured value: C: 72.20%, H: 4.80%, N: 14.87%.

EXAMPLE 3

Syntheses of Compound (21), Compound (A-1)

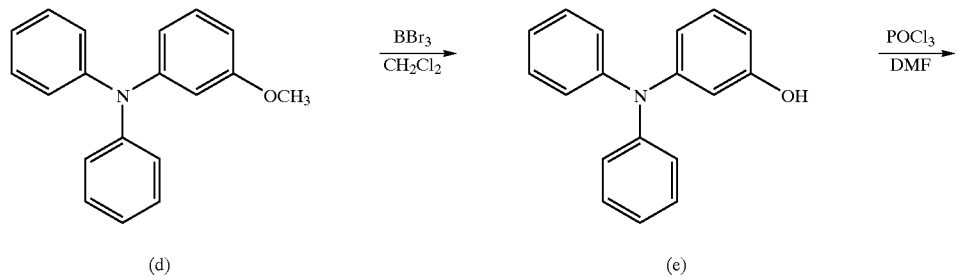

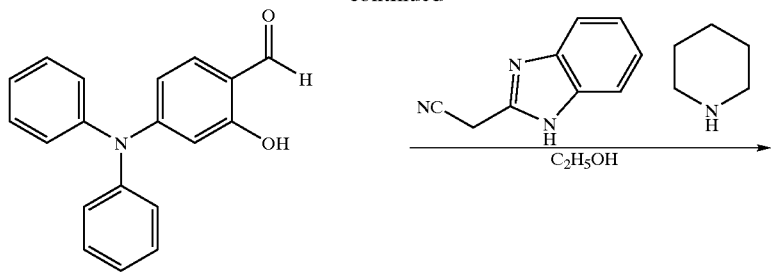

(f)

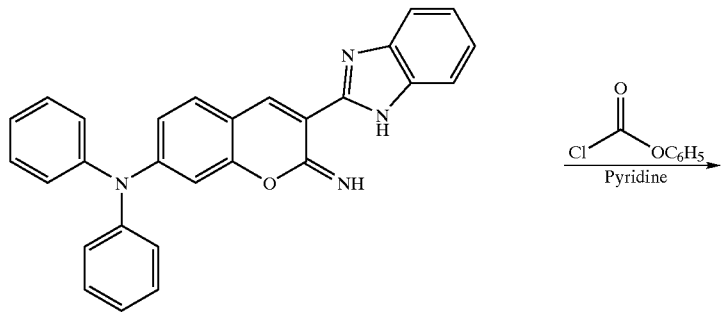

(A-1)

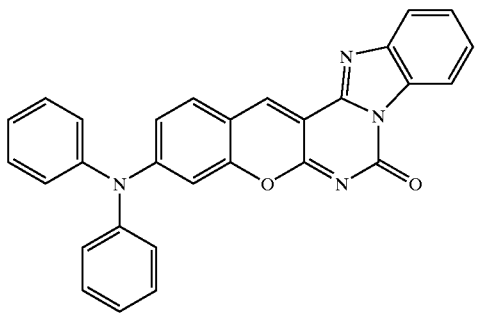

(21)

Synthesis of Compound (e)

3-Methoxyphenyldiphenylamine (5.5 g) was dissolved in 25 ml of dichloroethane and the solution was cooled to 0° C., and thereto was dropwise added 5.6 ml of $BBr_3$ slowly. After completion of dripping, the reaction solution was stirred at room temperature for 3 hours, then dropwise added into ice, and extracted with chloroform and an aqueous sodium hydroxide solution. The organic phase was concentrated, purified by silica gel column chromatography (hexane/ethyl acetate=19/1 (v/v)), thereby 4.2 g of Compound (e) was obtained (yield: 81%).

Synthesis of Compound (f)

Dimethylformamide (100 ml) was cooled to 0° C., then 18 ml of phosphorus oxychloride was dropwise added thereto. After termination of dripping, the reaction solution was stirred at room temperature for 30 minutes. A solution of 34.0 g of Compound (e) dissolved in 100 ml of dimethyl formamide was dropwise added to the above reaction solution, followed by stirring at room temperature for 12 hours. The reaction solution was dropwise added to water, and then extracted with chloroform and an aqueous sodium hydroxide solution. The organic phase was concentrated, purified by silica gel column chromatography (hexane/chloroform=8/2 (v/v)), thereby 22.5 g of Compound (f) was obtained (yield: 60%).

Synthesis of Compound (A-1)

Compound (f) (2.89 g), 1.57 g of 2-benzimidazolyl acetonitrile, 50 ml of ethanol and 0.2 ml of piperidine were put in a reaction vessel and refluxed with heating for 7 hours. Thereafter, the temperature of the reaction solution was lowered to room temperature, crystals precipitated were filtered out, washed with ethanol, and dried, thereby 3.4 g of Compound (A-1) was obtained (yield: 79%). The results of analysis of Compound (A-1) were as follows.

Absorption spectrum: Absorption maximum wavelength: 434 nm; (in chloroform); Fluorescence spectrum: Fluorescence maximum wavelength: 548 nm; (in chloroform).

Synthesis of Compound (21)

Pyridine (50 ml) was added to 3.0 g of Compound (A-1) and 1.3 ml of phenyl chloroformate was dropwise added thereto at room temperature under nitrogen atmosphere. After completion of dripping, the reaction solution was refluxed with heating for 6 hours, then the temperature of the solution was lowered to room temperature, crystals precipitated were filtered out, washed with ethanol, and dried, thereby 1.9 g of Compound (21) was obtained (yield: 60%). The results of analysis of Compound (21) were as follows.

$^1$H-NMR ($CDCl_3$) δ (ppm)=6.95 (2H, m), 7.20–7.58 (13H, m), 7.82 (1H, d), 7.48 (1H, d), 8.87 (1H, s)

EXAMPLE 4

Preparation and Evaluation of Luminous device

EXAMPLE 4-1

A transparent supporting substrate comprising a glass substrate of a size of 25 mm×25 mm×0.7 mm having coated thereon ITO in a thickness of 150 nm was used. After this transparent supporting substrate was subjected to etching and washing, 40 mg of poly(N-vinylcarbazole), 12 mg of PBD (2-(4-biphenylyl)-5-(4-tert-butylphenyl)-1,3,4-oxadiazole), and 0.5 mg of the compound described in Table 1 below were dissolved in 3 ml of 1,2-dichloroethane and spin-coated on the above-washed ITO substrate. The film thickness of the thus-formed organic thin layer was about 120 nm. A mask which had been subjected to patterning (a mask having an emission area of 5 mm×5 mm) was set up on the organic thin layer, and magnesium/silver in the ratio of 10/1 was co-deposited in a thickness of 50 nm in a vapor depositing apparatus, then silver was deposited in a thickness of 50 nm, thereby a luminous device was prepared.

Direct current constant voltage was impressed to the luminous device to effect emission using source measuring unit model 2400 manufactured by Toyo Technica Co., Ltd. The luminance was measured using luminometer BM-8 manufactured by Topcon Co., Ltd., and the luminescent wavelength and chromaticity coordinates were measured using spectrum analyzer PMA-11 manufactured by Hamamatsu Photonics Co., Ltd. Further, after the luminous device was allowed to stand under the conditions of 60° C., 20% RH for 3 hours, the presence of dark spots on the luminescent surface was evaluated (driving voltage: 15 V). The results obtained are shown in Table 1 below.

Comparative Compound A

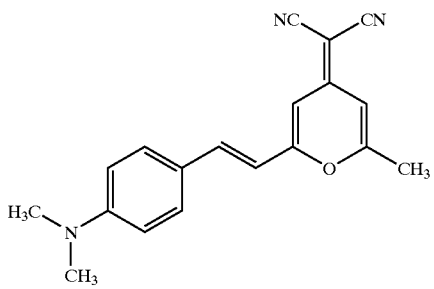

Comparitive Compound B

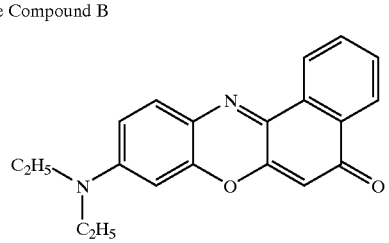

As is apparent from the results in Table 1, the devices in which the compounds according to the present invention were used were capable of high luminance emission with low voltage driving, and exhibited uniform planar emission property and excellent durability, and so generation of dark spots was less with the lapse of time as compared with the devices using the comparative compounds. In particular, according to the present invention good luminescent characteristics could be obtained in a coating process in general showing low emission luminance.

TABLE 1

| Sample No. | Compound | Minimum Driving Voltage (V) | Luminescent Wavelength λmax (nm) | Maximum Luminance (cd/m$^2$) | Generation of Dark Spots | Remarks |
|---|---|---|---|---|---|---|
| 1-1 | Comparative Compound A | 15 | 585 | 60 | Observed | Comparison |
| 1-2 | Comparative Compound B | 14 | 596 | 80 | Observed | Comparison |
| 1-3 | Exemplified Compound 1 | 9 | 560 | 150 | Not observed | Invention |
| 1-4 | Exemplified Compound 2 | 8 | 565 | 120 | Not observed | Invention |
| 1-5 | Exemplified Compound 3 | 9 | 570 | 280 | Not observed | Invention |
| 1-6 | Exemplified Compound 4 | 7 | 577 | 350 | Not observed | Invention |
| 1-7 | Exemplified Compound 5 | 7 | 579 | 210 | Not observed | Invention |
| 1-8 | Exemplified Compound 15 | 7 | 565 | 160 | Not observed | Invention |
| 1-9 | Exemplified Compound 21 | 6 | 610 | 460 | Not observed | Invention |

EXAMPLE 4-2

After ITO substrate was subjected to etching and washing in the same manner as in Example 4-1, about 40 nm of TPD (N,N'-bis(3-methylphenyl)-N,N'-diphenylbenzidine), about 20 nm of the compound shown in Table 2 below, and about 40 nm of 2,5-bis(1-naphthyl)-1,3,4-oxadiazole were vapor deposited in order in vacuo of $10^{-5}$ to $10^{-6}$ Torr under the substrate temperature condition of room temperature. Subsequently, vapor deposition of the cathode was performed in the same manner as in Example 4-1 to prepare a luminous device and evaluation was carried out. The results obtained are shown in Table 2 below. As is apparent from the results in Table 2, the devices in which the compounds according to the present invention were used were capable of high luminance emission also in a vapor deposition process as compared with the devices using the comparative compounds.

compound shown in Table 3 below and Alq (tris(8-hydroxyquinolinate)aluminum) were vapor deposited at depositing rate of 0.04 Å/sec and 4 Å/sec, respectively, in a film thickness of about 60 nm. Subsequently, deposition of the cathode was performed in the same manner as in Example 4-1 to prepare a luminous device and evaluation was carried out. The results obtained are shown in Table 3 below. As is apparent from the results in Table 3, the devices in which the compounds according to the present invention were used were capable of high luminance emission also with the doped system in a vapor deposition process as compared with the devices using the comparative compounds.

TABLE 2

| Sample No. | Compound | Minimum Driving Voltage (V) | Luminescent Wavelength λmax (nm) | Maximum Luminance (cd/m$^2$) | Generation of Dark Spots | Remarks |
|---|---|---|---|---|---|---|
| 2-1 | Comparative Compound A | 14 | 580 | 80 | Observed | Comparison |
| 2-2 | Comparative Compound B | 14 | 592 | 110 | Observed | Comparison |
| 2-3 | Exemplified Compound 1 | 9 | 588 | 240 | Not observed | Invention |
| 2-4 | Exemplified Compound 2 | 8 | 592 | 300 | Not observed | Invention |
| 2-5 | Exemplified Compound 3 | 7 | 595 | 440 | Not observed | Invention |
| 2-6 | Exemplified Compound 4 | 8 | 594 | 510 | Not observed | Invention |
| 2-7 | Exemplified Compound 5 | 6 | 600 | 400 | Not observed | Invention |
| 2-8 | Exemplified Compound 15 | 6 | 588 | 320 | Not observed | Invention |
| 2-9 | Exemplified Compound 21 | 6 | 610 | 630 | Not observed | Invention |

Comparative Compounds A and B were the same as those used in Example 4-1.

EXAMPLE 4-3

After ITO substrate was subjected to etching and washing in the same manner as in Example 4-1, TPD was vapor deposited in a thickness of about 40 nm, and then the

TABLE 3

| Sample No. | Compound | Minimum Driving Voltage (V) | Luminescent Wavelength λmax (nm) | Maximum Luminance (cd/m$^2$) | Generation of Dark Spots | Remarks |
|---|---|---|---|---|---|---|
| 3-1 | Comparative Compound A | 14 | 580 | 4,800 | Observed | Comparison |
| 3-2 | Comparative Compound B | 14 | 610 | 200 | Observed | Comparison |
| 3-3 | Exemplified Compound 1 | 9 | 560 | 10,000 | Not observed | Invention |
| 3-4 | Exemplified Compound 2 | 8 | 565 | 7,000 | Not observed | Invention |
| 3-5 | Exemplified Compound 3 | 7 | 570 | 8,500 | Not observed | Invention |
| 3-6 | Exemplified Compound 4 | 8 | 571 | 9,200 | Not observed | Invention |
| 3-7 | Exemplified Compound 5 | 6 | 577 | 9,000 | Not observed | Invention |
| 3-8 | Exemplified Compound 15 | 6 | 565 | 5,000 | Not observed | Invention |
| 3-9 | Exemplified Compound 21 | 6 | 612 | 11,000 | Not observed | Invention |

TABLE 3-continued

| Sample No. | Compound | Minimum Driving Voltage (V) | Luminescent Wavelength λmax (nm) | Maximum Luminance (cd/m$^2$) | Generation of Dark Spots | Remarks |
|---|---|---|---|---|---|---|

Comparative Compounds A and B were the same as those used in Example 4-1.

EXAMPLE 4-4

After ITO substrate was subjected to etching and washing in the same manner as in Example 4-1, TPD was vapor deposited in a thickness of about 40 nm, the compound shown in Table 4 below was deposited in a thickness of about 40 nm, and then Alq (tris(8-hydroxyquinolinate) aluminum) was deposited in a film thickness of about 20 nm. Subsequently, deposition of the cathode was performed in the same manner as in Example 4-1 to prepare a luminous device and evaluation was carried out. The results obtained are shown in Table 4 below.

TABLE 4

| Sample No. | Compound | Minimum Driving Voltage (V) | Luminescent Wavelength λmax (nm) | Maximum Luminance (cd/m$^2$) | Generation of Dark Spots | CIE Chromaticity Coordinates (X, Y) |
|---|---|---|---|---|---|---|
| 4-1 | Exemplified Compound 21 | 5 | 640 | 640 | Not observed | (0.69, 0.29) |
| 4-2 | Exemplified Compound 24 | 5 | 645 | 610 | Not observed | (0.69, 0.29) |
| 4-3 | Exemplified Compound A-1 | 5 | 550 | 1,200 | Not observed | (0.35, 0.49) |
| 4-4 | Exemplified Compound A-22 | 6 | 557 | 1,300 | Not observed | (0.35, 0.55) |

As is apparent from the results in Table 4, the devices in which the compounds according to the present invention were used were capable of high luminance emission also with the non-doped system in a vapor deposition process.

EXAMPLE 4-5

After ITO substrate was subjected to etching and washing in the same manner as in Example 4-1, the compound shown in Table 5 below was deposited in a thickness of about 60 nm, and then Alq (tris(8-hydroxyquinolinate)aluminum) was deposited in a film thickness of about 40 nm. Subsequently, deposition of the cathode was performed in the same manner as in example 4-1 to prepare a luminous device and evaluation was carried out. The results obtained are shown in Table 5 below.

TABLE 5

| Sample No. | Compound | Minimum Driving Voltage (V) | Luminescent Wavelength λmax (nm) | Maximum Luminance (cd/m$^2$) | Generation of Dark Spots | CIE Chromaticity Coordinates (X, Y) |
|---|---|---|---|---|---|---|
| 5-1 | Exemplified Compound 21 | 5 | 650 | 400 | Not observed | (0.68, 0.30) |
| 5-2 | Exemplified Compound 24 | 5 | 658 | 390 | Not observed | (0.69, 0.29) |
| 5-3 | Exemplified Compound A-1 | 5 | 555 | 980 | Not observed | (0.35, 0.49) |
| 5-4 | Exemplified Compound A-22 | 6 | 560 | 1,010 | Not observed | (0.35, 0.55) |

As is apparent from the results in Table 5, the compound according to the present invention is effective as a positive hole-injecting-transporting agent and luminous material in one, and exhibits high luminance emission.

EXAMPLE 21

Preparation and Evaluation of Luminous device

A transparent supporting substrate comprising a glass substrate of a size of 25 mm×25 mm×0.7 mm having coated thereon ITO in a thickness of 150 nm (manufactured by Tokyo Sanyo Shinku Co., Ltd.) was used. After this transparent supporting substrate was subjected to etching and washing, 40 mg of poly(N-vinylcarbazole), 12 mg of PBD (2-(4-biphenylyl)-5-(4-tert-butylphenyl)-1,3,4-oxadiazole), and 0.5 mg of the compound described in Table 21 below were dissolved in 3 ml of 1,2-dichloroethane and spin-coated on the above-washed ITO substrate. The film thickness of the thus-formed organic thin layer was about 120 nm. A mask which had been subjected to patterning (a mask having an emission area of 5 mm×5 mm) was set up on the organic thin layer, and magnesium/silver in the ratio of 10/1 was co-deposited in a thickness of 50 nm in a vapor depositing apparatus, then silver was deposited in a thickness of 50 nm, thereby a luminous device was prepared.

Direct current constant voltage was impressed to the luminous device to effect emission using source measuring unit model 2400 manufactured by Toyo Technica Co., Ltd. The luminance was measured using luminometer BM-8 manufactured by Topcon Co., Ltd., and the luminescent wavelength and CIE chromaticity coordinates were measured using spectrum analyzer PMA-11 manufactured by Hamamatsu Photonics Co., Ltd. Further, after the luminous device was allowed to stand under the conditions of 60° C., 20% RH for 3 hours, the presence of dark spots on the luminescent surface was evaluated (driving voltage: 15 V). The results obtained are shown in Table 21 below.

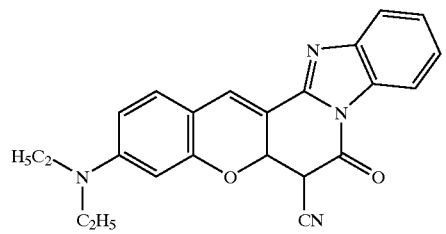

Comparative Compound C

As is apparent from the results in Table 21, the devices in which the compounds according to the present invention were used were capable of high luminance emission with low voltage driving, and exhibited uniform planar emission property and excellent durability, and so generation of dark spots was less with the lapse of time as compared with the devices using Comparative Compounds A and B and with the device using Comparative Compound C disclosed in JP-A-6-228544 (the term "JP-A" as used herein means an "unexamined published Japanese patent application"). In particular, according to the present invention good luminescent characteristics could be obtained in a coating process in showing low emission luminance.

TABLE 21

| Sample No. | Compound | Minimum Driving Voltage (V) | Luminescent Wavelength λmax (nm) | Maximum Luminance (cd/m$^2$) | Generation of Dark Spots | Remarks |
|---|---|---|---|---|---|---|
| 21-1 | Comparative Compound A | 15 | 585 | 60 | Observed | Comparison |
| 21-2 | Comparative Compound B | 14 | 596 | 120 | Observed | Comparison |
| 21-3 | Comparative Compound C | 15 | 586 | 500 | Observed | Comparison |
| 21-4 | Exemplified Compound 1' | 11 | 560 | 750 | Not observed | Invention |
| 21-5 | Exemplified Compound 2' | 10 | 565 | 820 | Not observed | Invention |
| 21-6 | Exemplified Compound 3' | 10 | 565 | 900 | Not observed | Invention |
| 21-7 | Exemplified Compound 6' | 7 | 620 | 1,200 | Not observed | Invention |
| 21-8 | Exemplified Compound 10' | 7 | 625 | 1,100 | Not observed | Invention |

EXAMPLE 22

After ITO substrate was subjected to etching and washing in the same manner as in Example 21, about 40 nm of TPD (N,N'-bis(3-methylphenyl)-N,N'-diphenylbenzidine), about 20 nm of the compound shown in Table 22 below, and about 40 nm of 2,5-bis(1-naphthyl)-1,3,4-oxadiazole were vapor deposited in order in vacuo of $10^{-5}$ to $10^{-6}$ Torr under the substrate temperature condition of room temperature. Subsequently, vapor deposition of the cathode was performed in the same manner as in Example 21 to prepare a luminous device and evaluation was carried out. The results obtained are shown in Table 22 below. As is apparent from the results in Table 22, in the devices in which the compounds according to the present invention were used, generation of dark spots with the lapse of time was less, and showed high luminance emission also in a vapor deposition process as compared with the devices using the comparative compounds.

TABLE 22

| | Minimum Driving | Luminescent Wavelength | Maximum | Generation |

| Sample No. | Compound | Voltage (V) | λmax (nm) | Luminance (cd/m$^2$) | of Dark Spots | Remarks |
|---|---|---|---|---|---|---|
| 22-1 | Comparative Compound A | 14 | 580 | 80 | Observed | Comparison |
| 22-2 | Comparative Compound B | 14 | 592 | 110 | Observed | Comparison |
| 22-3 | Comparative Compound C | 15 | 587 | 50 | Observed | Comparison |
| 22-4 | Exemplified Compound 6' | 8 | 635 | 2,000 | Not observed | Invention |
| 22-5 | Exemplified Compound 8' | 6 | 630 | 2,100 | Not observed | Invention |
| 22-6 | Exemplified Compound 9' | 7 | 640 | 2,100 | Not observed | Invention |
| 22-7 | Exemplified Compound 10' | 8 | 645 | 2,500 | Not observed | Invention |
| 22-8 | Exemplified Compound 11' | 6 | 645 | 2,300 | Not observed | Invention |

Comparative Compounds A, B and C were the same as those used in Example 21.

EXAMPLE 23

After ITO substrate was subjected to etching and washing in the same manner as in Example 21, TPD was vapor deposited in a thickness of about 40 nm, and then the compound shown in Table 23 below and Alq (tris(8-hydroxyquinolinate)aluminum) were vapor deposited at depositing rate of 0.04 Å/sec and 4 Å/sec, respectively, in a film thickness of about 60 nm. Subsequently, deposition of the cathode was performed in the same manner as in Example 21 to prepare a luminous device and evaluation was carried out. The results obtained are shown in Table 23 below. As is apparent from the results in Table 23, the devices in which the compounds according to the present invention were used could exhibit high color purity and high luminance emission also with the doped system in a vapor deposition process as compared with the devices using the comparative compounds.

20 nm. Subsequently, deposition of the cathode was performed in the same manner as in Example 21 to prepare a luminous device and evaluation was carried out. Minimum driving voltage was 6 V, maximum luminance at driving voltage 18 V was 720 cd/m$^2$, λmax=640 nm, and CIE chromaticity coordinates (x, y)=(0.69, 0.29). Generation of dark spots was not observed.

As is apparent from these results, the device according to the present invention exhibited high luminance emission also with the non-doped system in a vapor deposition process.

EXAMPLE 25

After ITO substrate was subjected to etching and washing in the same manner as in Example 21, exemplified Compound 6' was vapor deposited in a thickness of about 60 nm, and then Alq (tris(8-hydroxyquinolinate)aluminum) was

TABLE 23

| Sample No. | Compound | Minimum Driving Voltage (V) | Luminescent Wavelength λmax (nm) | Maximum Luminance (cd/m$^2$) | Generation of Dark Spots | CIE Chromaticity Coordinates (X, Y) |
|---|---|---|---|---|---|---|
| 23-1 | Comparative Compound A | 14 | 580 | 4,800 | Observed | (0.55, 0.44) |
| 23-2 | Comparative Compound B | 14 | 610 | 200 | Observed | (0.65, 0.34) |
| 23-3 | Exemplified Compound C | 15 | 590 | 5,000 | Observed | (0.61, 0.37) |
| 23-4 | Exemplified Compound 6' | 9 | 630 | 7,000 | Not observed | (0.67, 0.32) |
| 23-5 | Exemplified Compound 8' | 9 | 620 | 9,000 | Not observed | (0.66, 0.33) |
| 23-6 | Exemplified Compound 9' | 9 | 630 | 10,000 | Not observed | (0.67, 0.32) |
| 23-7 | Exemplified Compound 10' | 8 | 635 | 12,000 | Not observed | (0.68, 0.31) |
| 23-8 | Exemplified Compound 11' | 7 | 635 | 10,000 | Not observed | (0.68, 0.31) |

Comparative Compounds A, B and C were the same as those used in Example 21.

EXAMPLE 24

After ITO substrate was subjected to etching and. washing in the same manner as in Example 21, TPD was vapor deposited in a thickness of about 40 nm, and then exemplified Compound 6' and Alq (tris(8-hydroxyquinolinate) aluminum) were vapor deposited at depositing rate of 0.04 Å/sec and 4 Å/sec, respectively, in a film thickness of about vapor deposited in a film thickness of about 40 nm. Subsequently, deposition of the cathode was performed in the same manner as in Example 21 to prepare a luminous device and evaluation was carried out. Minimum driving voltage was 5 V, maximum luminance at driving voltage 18 V was 400 cd/m$^2$, and λmax 640 nm.

As is apparent from these results, the device according to the present invention is effective as a positive hole-injectingtransporting agent and luminous material in one, and exhibits high luminance emission.

According to the present invention, a luminous device capable of high luminance emission with low voltage driving and having long life as compared with conventional luminous devices can be obtained. Further, a luminous device also showing good color purity can be obtained according to the present invention. By using the compound of the present invention, high efficiency and high luminous emission can be attained even with a non-doped type device. In particular, excellent luminescent characteristics can be obtained even in a coating system where luminance is in general low, therefore, advantageous device production can be realized from the viewpoint of the production cost.

While the invention has been described in detail and with reference to specific examples thereof, it will be apparent to one skilled in the art that various changes and modifications can be made therein without departing from the spirit and scope thereof.

What is claimed is:

1. A luminous device comprising:

a pair of electrodes; and at least one organic compound thin layer including a luminous layer, provided between the electrodes, wherein at least one layer of said organic compound thin layer(s) contains at least one compound selected from:

compounds represented by formula (1):

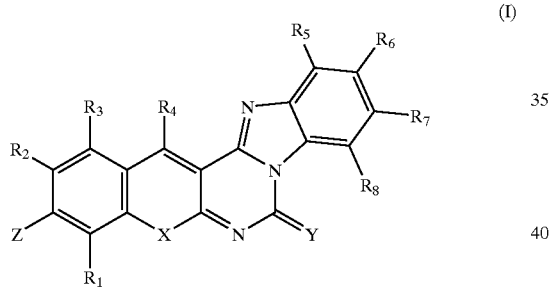

(I)

wherein $R_1$, $R_2$, $R_3$, $R_4$, $R_5$, $R_6$, $R_7$ and $R_8$ each represents a hydrogen atom or a substituent; X represents O, S or N—R, wherein R represents a hydrogen atom, an aliphatic hydrocarbon group, an aryl group or a heterocyclic group; Y represents O, S or $CQ_1(Q_2)$, wherein $Q_1$ and $Q_2$ each represents a hydrogen atom or a substituent, at least either one of them represents an electron attractive group, and $Q_1$ and $Q_2$ may be linked to each other to form a ring; and Z is represented by the following formula (II):

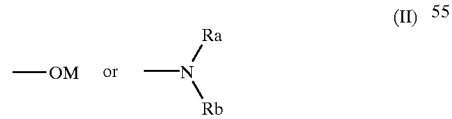

(II)

wherein $R_a$ and $R_b$ each represents a hydrogen atom, an aliphatic hydrocarbon group, an aryl group or a heterocyclic group, and at least one combination of $R_a$ and $R_b$, $R_a$ and $R_1$, and $R_b$ and $R_2$ may be linked to each other to form a ring; M represents a hydrogen atom, an aliphatic hydrocarbon group, an aryl group, a heterocyclic group or a cation;

compounds represented by formula (I-a):

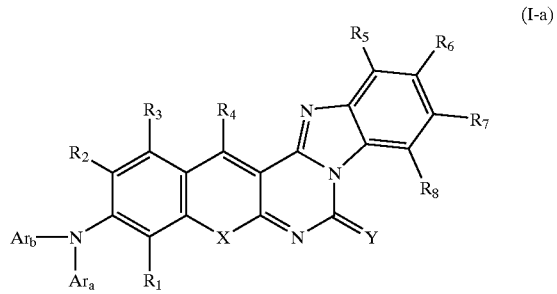

(I-a)

wherein $R_1$, $R_2$, $R_3$, $R_4$, $R_5$, $R_6$, $R_7$ and $R_8$ each represents a hydrogen atom or a substituent; X represents O, S or N—R, wherein R represents a hydrogen atom, an aliphatic hydrocarbon group, an aryl group or a heterocyclic group; $Ar_a$ and $Ar_b$ each represents an aryl group or an aromatic heterocyclic group, and at least one combination of $Ar_a$ and $Ar_b$, $Ar_a$ and $R_1$, and $Ar_b$ and $R_2$ may be linked to each other to form a ring; and Y represents O or S;

compounds represented by formula (III):

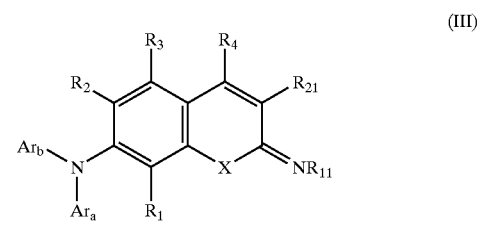

(III)

wherein $R_1$, $R_2$, $R_3$ and $R_4$ each represents a hydrogen atom or a substituent; $R_{11}$ represents a hydrogen atom, an aliphatic hydrocarbon group, an aryl group or a heterocyclic group; $R_{21}$, represents a hydrogen atom or a substituent; X represents O, S or N—R, wherein R represents a hydrogen atom, an aliphatic hydrocarbon group, an aryl group or a heterocyclic group; and $Ar_a$ and $Ar_b$ each represents an aryl group or an aromatic heterocyclic group, and at least one combination of $Ar_a$ and $Ar_b$, $Ar_a$ and $R_1$, and $Ar_b$ and $R_2$ may be linked to each other to form a ring; and compounds represented by formula (I'):

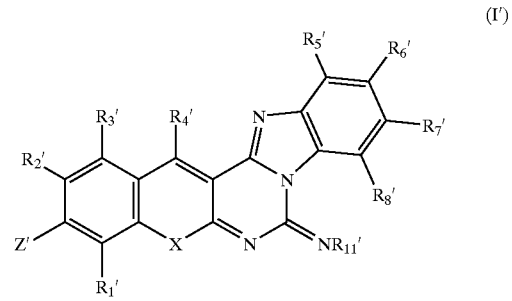

(I')

wherein $R_1'$, $R_2'$, $R_3'$, $R_4'$, $R_5'$, $R_6'$, $R_7'$, $R_8'$ and $R_{11}'$ each represents a hydrogen atom or a substituent; X' represents O, S or N—R', wherein R' represents a hydrogen atom, an aliphatic hydrocarbon group, an aryl group or a heterocyclic group; and Z' represents N—Ra' Rb' (wherein Ra' and Rb' each represents a hydrogen atom, an aliphatic hydrocarbon group, an aryl group or a heterocyclic group or —OM' (wherein M' represents a hydrogen atom, an aliphatic hydrocarbon group, an aryl group, a heterocyclic group or a cation).

2. The luminous device according to claim 1, wherein said layer containing at least one compound of formula (I), (I-a), (III) or (I') further comprises a polymer, said at least one compound being dispersed in the polymer.

3. The luminous device according to claim 1, wherein said at least one compound comprises a compound of formula (I), (I-a) or (III).

4. The luminous device according to claim 1, wherein said at least one compound comprises a compound of formula (I').

* * * * *